United States Patent
Callahan

(10) Patent No.: US 11,986,570 B2
(45) Date of Patent: May 21, 2024

(54) PORTABLE WAND SYSTEMS AND METHODS OF USING THE SAME TO INDICATE AND VERIFY SURFACE TREATMENT APPLICATIONS

(71) Applicant: The Boeing Company, Chicago, IL (US)

(72) Inventor: Kevin S. Callahan, Shoreline, WA (US)

(73) Assignee: The Boeing Company, Arlington, VA (US)

( * ) Notice: Subject to any disclaimer, the term of this patent is extended or adjusted under 35 U.S.C. 154(b) by 381 days.

(21) Appl. No.: 16/990,908

(22) Filed: Aug. 11, 2020

(65) Prior Publication Data

US 2022/0023479 A1    Jan. 27, 2022

Related U.S. Application Data

(60) Provisional application No. 63/055,801, filed on Jul. 23, 2020.

(51) Int. Cl.
*A61L 2/28* (2006.01)
*A61L 2/10* (2006.01)
*A61L 2/24* (2006.01)

(52) U.S. Cl.
CPC .................................. *A61L 2/28* (2013.01); *A61L 2/10* (2013.01); *A61L 2/24* (2013.01); *A61L 2202/14* (2013.01); *A61L 2202/25* (2013.01)

(58) Field of Classification Search
CPC ................. A61L 2/10; A61L 2/28; A61L 2/24
See application file for complete search history.

(56) References Cited

U.S. PATENT DOCUMENTS 9,272,058 B1    3/2016  Montgomery
2004/0090333 A1*    5/2004  Wildman ............. G08B 21/245
340/573.1

(Continued)

FOREIGN PATENT DOCUMENTS

AU    2015346482 A1    6/2017
CN    107532959    *    1/2018
EP    3915595 A2    12/2021

(Continued)

OTHER PUBLICATIONS

Extended European Search Report (EESR), European Patent Office, dated Dec. 15, 2021, for Application No. EP21180276.4, Applicant The Boeing Company, 8 pages.

(Continued)

*Primary Examiner* — Donald R Spamer
*Assistant Examiner* — Priscilla Browning

(57) ABSTRACT

There is provided a portable wand system including a wand applicator containing a surface treatment application element. The portable wand system further includes a wand controller subsystem coupled to the wand applicator. The wand controller subsystem includes a computer program, and a depiction of one or more surfaces to be surface treated with the surface treatment application element. The portable wand system further includes a user input button coupled to the wand applicator, an indicator element, a power assembly coupled to the wand controller subsystem, and one or more registration features to register the wand applicator against known location(s) at the one or more surfaces in the depiction. The portable wand system measures positional data of the wand applicator in real-time, and compares the positional data against the depiction, to indicate to a user when a predetermined surface treatment application is achieved for the one or more surfaces.

20 Claims, 19 Drawing Sheets

(56) References Cited

U.S. PATENT DOCUMENTS

| | | | | |
|---|---|---|---|---|
| 2006/0216193 | A1* | 9/2006 | Johnson | A61L 2/24 250/504 R |
| 2010/0028201 | A1* | 2/2010 | Neister | A61L 2/10 73/29.02 |
| 2010/0104471 | A1 | 4/2010 | Harmon et al. | |
| 2010/0258681 | A1* | 10/2010 | Chen | B64C 39/001 244/34 A |
| 2010/0324723 | A1* | 12/2010 | Zech | B67C 3/007 700/223 |
| 2012/0280147 | A1* | 11/2012 | Douglas | A61L 2/10 250/492.1 |
| 2012/0282135 | A1* | 11/2012 | Trapani | A61L 2/24 422/291 |
| 2016/0089457 | A1* | 3/2016 | Liao | G06F 1/1684 250/504 R |
| 2020/0179543 | A1* | 6/2020 | Deshays | A61L 2/24 |

FOREIGN PATENT DOCUMENTS

| | | | | |
|---|---|---|---|---|
| EP | 3915596 | A2 | 12/2021 | |
| WO | WO-2020081351 | A1 * | 4/2020 | ............ A01B 69/00 |
| WO | 2020195017 | A1 | 10/2020 | |

OTHER PUBLICATIONS

Extended European Search Report (EESR), European Patent Office, dated Feb. 28, 2022, for related Application No. EP21194416.0, Applicant The Boeing Company, 5 pages.

European Patent Office (EPO) Office Action, dated Feb. 8, 2023, for Counterpart EP Application No. 21180276.4, Applicant The Boeing Company, 4 pages.

European Patent Office (EPO) Office Action, dated Oct. 12, 2023, for related EP Application No. 21180276.4, Applicant The Boeing Company, 4 pages.

* cited by examiner

_PORTABLE WAND SYSTEMS AND METHODS OF USING THE SAME TO INDICATE AND VERIFY SURFACE TREATMENT APPLICATIONS_

CROSS-REFERENCE TO RELATED APPLICATION

The present application is a non-provisional application and claims priority to provisional application Ser. No. 63/055,801, filed Jul. 23, 2020, entitled PORTABLE WAND SYSTEMS AND METHODS OF USING THE SAME TO INDICATE AND VERIFY SURFACE TREATMENT APPLICATIONS, the entire contents of which is incorporated herein by reference.

FIELD

The disclosure relates generally to systems and methods for indicating and verifying surface treatment applications, and more particularly, to systems and methods for indicating and verifying that disinfection, sanitization, and other surface treatment processes are sufficient and complete.

BACKGROUND

Manual processes for performing surface treatment applications, such as disinfecting or sanitizing surfaces, using handheld devices may have varying degrees of consistency, and repeatability may prove challenging. When a human operator performs such manual processes, it may be difficult to simultaneously maintain a high degree of quality control and efficiency. For example, manual processes using handheld ultraviolet (UV) light devices to disinfect or sanitize surfaces may require spending longer treatment times to ensure complete surface treatment to account for operator variability. Even with generous processing margin allowances, it may still not be possible to thoroughly and reliably document complete coverage manually.

In addition, automated methods for performing surface treatment applications, such as disinfecting or sanitizing surfaces, may require highly complex equipment that is not generally as dexterous as a human operator, when a complex surface is to be surface treated.

Accordingly, there is a need for a portable, or handheld, system and method for performing surface treatment applications, such as disinfection, sanitization, and other surface treatment processes, that indicate and verify to a user when a surface has been sufficiently treated with a manual surface treatment process, that maintain a high degree of quality control and efficiency, and that provide advantages over known systems and methods.

SUMMARY

Example implementations of the present disclosure provide portable wand systems and methods of using the same to indicate and verify surface treatment applications. As discussed in the below detailed description, versions of the systems and methods may provide significant advantages over known systems and methods.

In a version of the disclosure, there is provided a portable wand system. The portable wand system comprises a wand applicator containing a surface treatment application element. The portable wand system further comprises a wand controller subsystem coupled to the wand applicator. The wand controller subsystem comprises a computer program, and a depiction of one or more surfaces to be surface treated with a surface treatment application of the surface treatment application element.

The portable wand system further comprises a user input button coupled to the wand applicator. The portable wand system further comprises an indicator element. The portable wand system further comprises a power assembly coupled to the wand applicator.

The portable wand system further comprises one or more registration features to register the wand applicator against one or more known locations at the one or more surfaces in the depiction. The portable wand system measures positional data of the wand applicator in real-time, and compares the positional data against the depiction, to indicate to a user when a predetermined surface treatment application is achieved for the one or more surfaces.

In another version of the disclosure, there is provided a portable wand system for disinfecting one or more surfaces in an interior of an aircraft. The portable wand system comprises a wand applicator containing an ultraviolet (UV) lamp element. The portable wand system further comprises a wand controller subsystem coupled to the wand applicator. The wand controller subsystem comprises a computer program, and a depiction of the one or more surfaces to be disinfected with the UV lamp element.

The portable wand system further comprises a user input button coupled to the wand applicator. The portable wand system further comprises an indicator element. The portable wand system further comprises a power assembly coupled to the wand applicator.

The portable wand system further comprises one or more registration features to register the wand applicator against one or more known locations on the one or more surfaces in the depiction. The portable wand system measures positional data of the wand applicator in real-time, and compares the positional data against the depiction, to indicate to a user when a predetermined ultraviolet (UV) light disinfection is achieved for the one or more surfaces.

In another version of the disclosure, there is provided a method for indicating to a user when a predetermined surface treatment application is achieved for one or more surfaces. The method comprises the step of providing a portable wand system. The portable wand system comprises a wand applicator containing a surface treatment application element. The portable wand system further comprises a wand controller subsystem coupled to the wand applicator. The wand controller subsystem comprises a computer program, and a depiction of the one or more surfaces to be surface treated with a surface treatment application of the surface treatment application element.

The portable wand system further comprises a user input button coupled to the wand applicator. The portable wand system further comprises an indicator element. The portable wand system further comprises a power assembly coupled to the wand applicator. The portable wand system further comprises one or more registration features to register the wand applicator against one or more known locations at the one or more surfaces in the depiction.

The method further comprises the step of pressing, by the user, the user input button to identify, with one of the one or more registration features, a starting position at one of the one or more surfaces to be surface treated. The method further comprises the step of measuring, with the portable wand system, positional data of the wand applicator in real-time. The method further comprises the step of activating, with the portable wand system, the surface treatment application element.

The method further comprises the step of moving, by the user, the wand applicator over the one or more surfaces to be surface treated, to treat the one or more surfaces with the surface treatment application element. The method further comprises the step of comparing, with the portable wand system, the positional data against the depiction.

The method further comprises the step of determining, with the portable wand system, when the predetermined surface treatment application is achieved with the surface treatment application element for the one or more surfaces. The method further comprises the step of activating, with the portable wand system, the indicator element to signal to the user that the predetermined surface treatment application is achieved with the surface treatment application element for the one or more surfaces.

In another version of the disclosure, there is provided a method for indicating to a user when a predetermined ultraviolet (UV) light disinfection is achieved for one or more surfaces in an interior of an aircraft. The method comprises the step of providing a portable wand system. The portable wand system comprises a wand applicator containing an ultraviolet (UV) lamp element. The portable wand system further comprises a wand controller subsystem coupled to the wand applicator. The wand controller subsystem comprises a computer program, and a depiction of the one or more surfaces to be disinfected with the UV lamp element.

The portable wand system further comprises a user input button coupled to the wand applicator. The portable wand system further comprises an indicator element. The portable wand system further comprises a power assembly coupled to the wand applicator. The portable wand system further comprises one or more registration features to register the wand applicator against one or more known locations at the one or more surfaces in the depiction.

The method further comprises the step of pressing, by the user, the user input button to identify, with one of the one or more registration features, a starting position at one of the one or more surfaces to be disinfected. The method further comprises the step of measuring, with the portable wand system, positional data of the wand applicator in real-time. The method further comprises the step of activating, with the portable wand system, the UV lamp element.

The method further comprises the step of moving, by the user, the wand applicator over the one or more surfaces to be disinfected with the UV lamp element. The method further comprises the step of comparing, with the portable wand system, the positional data against the depiction.

The method further comprises the step of determining, with the portable wand system, when the predetermined UV light disinfection is achieved with the UV lamp element for the one or more surfaces. The method further comprises the step of activating, with the portable wand system, the indicator element to signal to the user that the predetermined UV light disinfection is achieved with the UV lamp element for the one or more surfaces.

In another version of the disclosure, there is provided a portable wand system for performing a surface treatment application on one or more surfaces. The portable wand system comprises a system case. The portable wand system further comprises a wand applicator comprising a housing that houses an ultraviolet (UV) lamp element and an ultraviolet (UV) lamp sensor. The wand applicator is attached to the system case, via a hose. The hose has a first end attached to the wand applicator, and has a second end attached to a fan positioned in the system case.

The portable wand system further comprises a wand controller subsystem coupled to the wand applicator. The wand controller subsystem is positioned in the system case, and comprises a computer program, and a depiction of the one or more surfaces to be disinfected with the UV lamp element. The portable wand system further comprises a user input button coupled to the wand applicator. The portable wand system further comprises an indicator element. The portable wand system further comprises a power assembly coupled to the wand applicator, and positioned in the system case.

The portable wand system further comprises one or more registration features to register the wand applicator against one or more known locations on the one or more surfaces in the depiction. The portable wand system measures positional data of the wand applicator in real-time, and compares the positional data against the depiction, to indicate to a user when a predetermined surface treatment application is achieved for the one or more surfaces.

The features, functions, and advantages that have been discussed can be achieved independently in various versions of the disclosure or may be combined in yet other versions further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary versions, but which are not necessarily drawn to scale. The drawings are examples and not meant as limitations on the description or claims.

The figures shown in this disclosure represent various aspects of the versions presented, and only differences will be discussed in detail.

DETAILED DESCRIPTION

Disclosed versions or embodiments will now be described more fully hereinafter with reference to the accompanying drawings, in which some, but not all of the disclosed versions are shown. Indeed, several different versions may be provided and should not be construed as limited to the versions set forth herein. Rather, these versions are provided so that this disclosure will be thorough and fully convey the scope of the disclosure to those skilled in the art.

This specification includes references to "one version" or "a version". The instances of the phrases "in one version" or "in a version" do not necessarily refer to the same version. Particular features, structures, or characteristics may be combined in any suitable manner consistent with this disclosure.

As used herein, "comprising" is an open-ended term, and as used in the claims, this term does not foreclose additional structure or steps.

As used herein, "configured to" means various parts or components may be described or claimed as "configured to" perform a task or tasks. In such contexts, "configured to" is used to connote structure by indicating that the parts or components include structure that performs those task or tasks during operation. As such, the parts or components can be said to be configured to perform the task even when the specified part or component is not currently operational (e.g., is not on).

As used herein, the terms "first", "second", etc., are used as labels for nouns that they precede, and do not imply any type of ordering (e.g., spatial, temporal, logical, etc.).

As used herein, an element or step recited in the singular and preceded by the word "a" or "an" should be understood as not necessarily excluding the plural of the elements or steps.

Figure 1A:
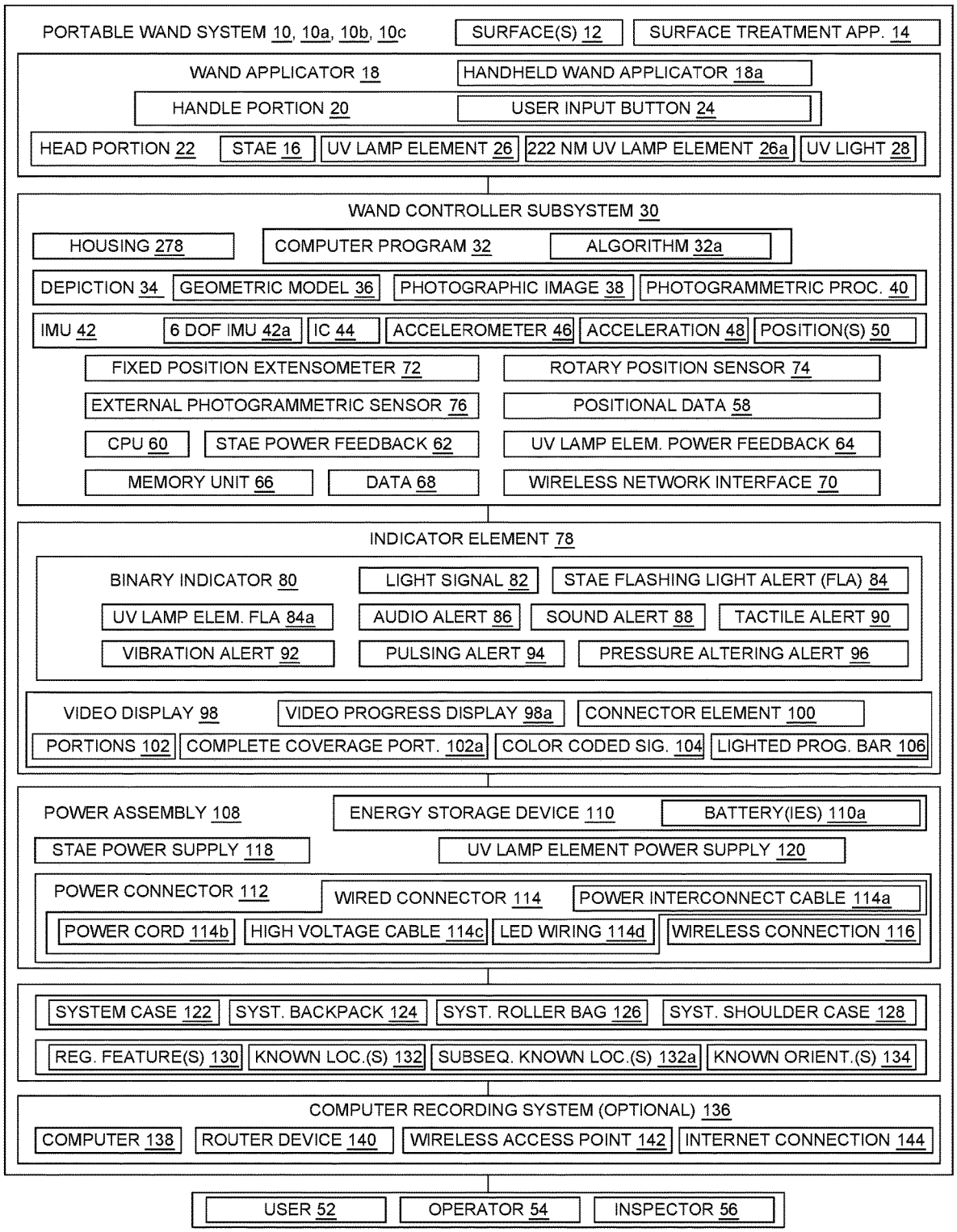
FIG. 1A is an illustration of a functional block diagram showing exemplary versions of a portable wand system of the disclosure.
Figure 1B:
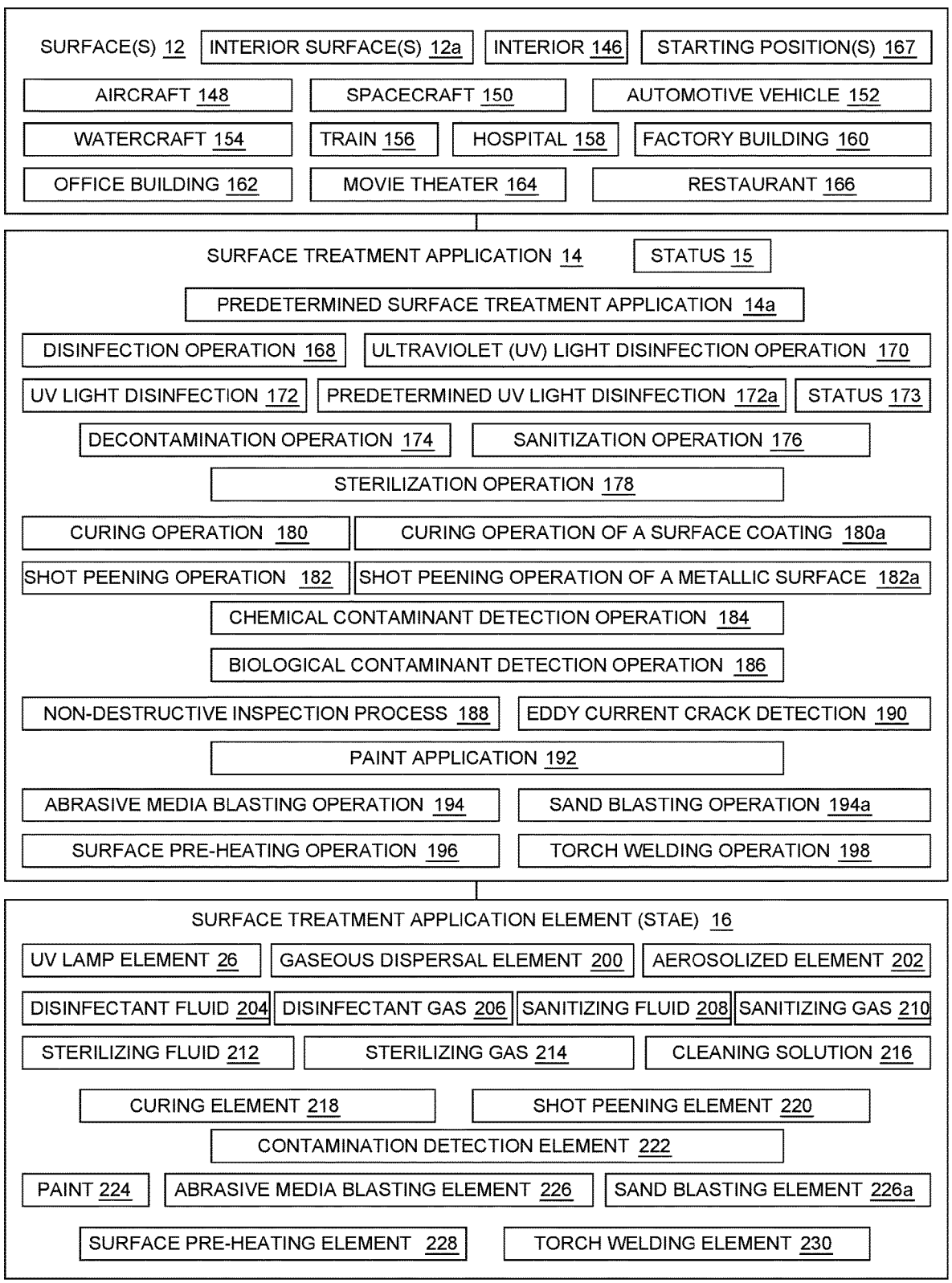
FIG. 1B is an illustration of a functional block diagram showing exemplary versions of surfaces, surface treatment applications, and surface treatment application elements used with exemplary versions of a portable wand system of the disclosure.

Now referring to the Figures, FIG. 1A is an illustration of a functional block diagram showing exemplary versions of a portable wand system 10 of the disclosure, and FIG. 1B is an illustration of a functional block diagram showing exemplary versions of surfaces 12, surface treatment applications 14, and surface treatment application elements (STAE) 16 used with exemplary versions of the portable wand system 10 of the disclosure. The portable wand system 10 is used to manually surface treat one or more surfaces 12 with a surface treatment application 14. The portable wand system 10 indicates, verifies, and validates that the correct, complete, and thorough application of the surface treatment application 14, such as an ultraviolet (UV) light disinfection operation 170 (see FIG. 1B), onto one or more surfaces 12 of an area or object, has been achieved. The portable wand system 10 also allows a user 52 (see FIG. 1A), such as an operator 54 (see FIG. 1A), to self-verify that the surface treatment application 14 has been sufficiently performed and completed.

The blocks in FIGS. 1A-1B represent elements, and lines connecting the various blocks do not imply any particular dependency of the elements. Furthermore, the connecting lines shown in the various Figures contained herein are intended to represent example functional relationships and/or physical couplings between the various elements, but it is noted that other alternative or additional functional relationships or physical connections may be present in versions disclosed herein.

As shown in FIG. 1A, in a version of the disclosure, there is provided the portable wand system 10. As shown in FIG. 1A, the portable wand system 10 comprises a wand applicator 18. Preferably, the wand applicator 18 is a handheld wand applicator 18a (see FIG. 1A) that is manually used by a user 52. The wand applicator 18 has a handle portion 20 (see FIG. 1A) and a head portion 22 (see FIG. 1A). The portable wand system 10 further comprises a user input button 24 (see FIG. 1A), or operator input button, coupled to the wand applicator 18. Preferably, the user input button 24 is coupled to, or integrated in, the handle portion 20 of the wand applicator 18.

The wand applicator 18, and in particular, the head portion 22 of the wand applicator 18, contains the surface treatment application element (STAE) 16. In a preferred version, the surface treatment application element (STAE) 16 comprises an ultraviolet (UV) lamp element 26. The UV lamp element 26 is operable to, or configured to, emit an ultraviolet (UV) light 28 (see FIG. 1A) having a wavelength in a range between 200 nm (nanometers) to 280 nm (nanometers), to sufficiently disinfect the one or more surfaces 12. More preferably, the UV lamp element 26 comprises a 222 nm (nanometer) UV lamp element 26a (see FIG. 1A), where the UV lamp element 26 is operable to, or configured to, emit the UV light 28 having a wavelength of 222 nanometers. Other versions of the surface treatment application element (STAE) 16 are discussed below with respect to FIG. 1B.

The UV light 28 used is preferably ultraviolet C (UVC) light that is short-wave and germicidal, and can emit sanitizing UV light 28. It has been found that sanitizing UV light having a wavelength of 222 nm (nanometers) kills or deactivates pathogens, such as viruses and bacteria, and is safe for human exposure. Further, the sanitizing UV light 28 having a wavelength of 222 nm may be emitted at full power within one millisecond, or less, of the UV lamp element 26 being activated.

As further shown in FIG. 1A, the portable wand system 10 further comprises a wand controller subsystem 30 coupled to the wand applicator 18, either wired or wirelessly. As shown in FIG. 1A, the wand controller subsystem 30 comprises a computer program 32, such as an algorithm 32a. As shown in FIG. 1A, the wand controller subsystem 30 further comprises a depiction 34, or image, of one or more surfaces 12 to be surface treated with the surface treatment application 14 of the surface treatment application element 16.

In one version, the depiction 34 comprises a geometric model 36, such as a CAD (computer-aided design) model, or another computer model, of one or more surfaces 12 to be surface treated with the surface treatment application 14 of the surface treatment application element 16. The geometric model 36 may comprise a model of an area with the one or more surfaces 12 and may comprise a map of a predetermined surface treatment application 14a (see FIG. 1B), or a desired or target surface treatment application, or dispensing coverage. In another version, the depiction 34 comprises a photographic image 38 (see FIG. 1A) obtained with a photogrammetric process 40 (see FIG. 1A).

As shown in FIG. 1A, the wand controller subsystem 30 may further comprise an inertial measurement unit (IMU) 42. Preferably, the IMU 42 comprises a 6 degrees of freedom inertial measurement unit (IMU) 42a (see FIG. 1A). As used herein, "6 degrees of freedom" means a freedom of movement in a three-dimensional space, where an object is free to change position as forward/backward, up/down, left/right translation in three perpendicular axes, combined with changes in orientation through rotation about three perpendicular axes, for example, yaw (normal axis), pitch (transverse axis), and roll (longitudinal axis).

The IMU 42 comprises an integrated circuit (IC) 44 (see FIG. 1A), and comprises an accelerometer 46 (see FIG. 1A) to measure an acceleration 48 (see FIG. 1A) of the wand applicator 18. The IMU 42 further measures one or more positions 50 (see FIG. 1A) of the wand applicator 18, as it is moved by a user 52 (see FIG. 1A), such as an operator 54 (see FIG. 1A), or an inspector 56 (see FIG. 1A), over the one or more surfaces 12 to be surface treated. The IMU 42 sends positional data 58 of movement of the wand applicator 18 to a central processing unit (CPU) 60 coupled to the IMU 42. The CPU 60 is part of the wand controller subsystem 30.

The wand controller subsystem 30 further comprises a surface treatment application element (STAE) power feedback 62 (see FIG. 1A) to the CPU 60. In a preferred version, where the portable wand system 10 includes the UV lamp element 26, the wand controller subsystem 30 further comprises an ultraviolet (UV) lamp element power feedback 64 (see FIG. 1A) to the CPU 60.

As shown in FIG. 1A, the wand controller subsystem 30 further comprises a memory unit 66 coupled to the CPU 60. The memory unit 66 stores data 68 (see FIG. 1A) measured by the portable wand system 10, including positional data 58 measured by the IMU 42. As shown in FIG. 1A, the wand controller subsystem 30 may further optionally comprise a wireless network interface 70 coupled to the CPU 60.

As an alternative to using the IMU 42 in the wand controller subsystem 30, the wand controller subsystem 30 may comprise separately, or in combination, one or more of, a fixed position extensometer 72 (see FIG. 1A), a rotary position sensor 74 (see FIG. 1A), and/or an external photogrammetric sensor 76 (see FIG. 1A). The fixed position extensometer 72 measures the elongation of a material under stress, and may also be used to determine yield strength, tensile strength, yield point elongation, strain-hardening exponent, and strain ratio. The rotary position sensor 74 measures rotational angles from output voltages and translates angular mechanical position to an electrical signal. The external photogrammetric sensor 76 records, measures, and interprets photographic images and patterns of electromagnetic radiant imagery and generates two-dimensional and three-dimensional digital models of the surface, area, or object as an end product.

As shown in FIG. 1A, the portable wand system 10 further comprises an indicator element 78. In one version, the indicator element 78 comprises a binary indicator 80 (see FIG. 1A), or on/off indicator. As shown in FIG. 1A, the binary indicator 80 comprises one of, a light signal 82 coupled to the wand applicator 18, a surface treatment application element (STAE) flashing light alert 84, such as an ultraviolet (UV) flashing light alert 84a, an audio alert 86, a sound alert 88, a tactile alert 90, a vibration alert 92, a pulsing alert 94, a pressure altering alert 96, or another suitable binary indicator, to indicate that the surface treatment application 14 of one or more of the one or more surfaces 12 is complete. The audio alert 86, or the sound alert 88, may comprise an audible bell, chime, beep, voice, or other sound or noise. The binary indicator 80 indicates that the surface treatment application 14, such as the predetermined surface treatment application 14a, of a sub-area, or one or more of the surfaces 12, is complete, and it is acceptable to continue to the next sub-area or surface 12.

As an alternative to the binary indicator 80, or in addition to the binary indicator 80, the portable wand system 10 may comprise a video display 98, such as a video progress display 98a, coupled to the wand applicator 18. In one version, the video display 98 may be coupled to the wand applicator 18, via a connector element 100 (see FIG. 1A), such as a wired interconnect cable, or a wireless connection. In another version, the video display 98 may be incorporated on the wand applicator 18. The video display 98 may comprise a handheld tablet computer coupled to the wand applicator 18, via the connector element 100, or may comprise a screen display incorporated on the wand applicator 18, or may comprise another suitable video display device. The video display 98 is visible to the user 52 (see FIG. 1A), and shows one or more of, portions 102 (see FIG. 1A) of the one or more surfaces 12 to be surface treated, and a color coded signal 104 (see FIG. 1A), comprising a lighted progress bar 106 (see FIG. 1A), or map, to indicate which portions 102 have complete coverage, such as complete coverage portions 102a (see FIG. 1A).

As shown in FIG. 1A, the portable wand system 10 further comprises a power assembly 108 coupled to the wand controller subsystem 30. As shown in FIG. 1A, the power assembly 108 comprises an energy storage device 110 coupled to a power connector 112. As shown in FIG. 1A, the energy storage device 110 may comprise one or more batteries 110a, or another suitable energy storage device. The power connector 112 may comprise a wired connector 114 (see FIG. 1A), such as a power interconnect cable 114a (see FIG. 1A), a power cord 114b (see FIG. 1A), a high voltage cable 114c (see FIG. 1A), LED (light-emitting diode) wiring 114d (see FIG. 1A), or another suitable wired connector. The power connector 112 may further comprise a wireless connector 116 (see FIG. 1A).

As shown in FIG. 1A, the power assembly 108 may further comprise a surface treatment application element (STAE) power supply 118, for example, a UV lamp element power supply 120, or another suitable power supply for a surface treatment application element 16.

As further shown in FIG. 1A, the portable wand system 10 may be transported, or carried, by a user 52 and/or stored in a system case 122, a system backpack 124, a system roller bag 126, a system shoulder case 128, or another suitable portable case, carrier, or bag.

As shown in FIG. 1A, the portable wand system 10 further comprises one or more registration features 130 to register the wand applicator 18 against one or more known locations 132 and/or known orientations 134 at the one or more surfaces 12 in the depiction 34, for example, in the geometric model 36.

As shown in FIG. 1A, the portable wand system may optionally further comprise a computer recording system 136 coupled to the wand controller subsystem 30. The computer recording system 136 is operable to, or configured to, analyze the positional data 58 of the wand applicator 18, and is operable to, or configured to, communicate to the indicator element 78 a status 15 (see FIG. 1B) of the surface treatment application 14, such as the predetermined surface treatment application 14a, on the one or more surfaces 12.

As shown in FIG. 1A, the computer recording system 136 comprises a computer 138 coupled to a router device 140 and a wireless access point 142, via an internet connection 144. The wireless network interface 70 of the wand controller subsystem 30 interfaces, or communicates, with the wireless access point 142 of the computer recording system 136. The CPU 60 converts streams of data 68 and may wirelessly transmit the positional data 58, based on the depiction 34, such as the geometric model 36, and duration, to the computer recording system 136. The computer recording system 136 verifies the location of the wand applicator 18, and calculates the position 50 of the wand applicator 18, and provides feedback as to what surfaces 12 still need to be surface treated with the surface treatment application element 16. The computer recording system 136 also provides a central recording function 242 (see FIGS. 3A-3B), as discussed below, to document and record complete coverage of the one or more surfaces 12 with the surface treatment application 14.

The portable wand system 10 measures positional data 58 of the wand applicator 18 in real-time, and compares the positional data 58 against the depiction 34, to indicate to a user 52 when a predetermined surface treatment application 14a (see FIG. 1B) is achieved for the one or more surfaces 12, and to indicate a sufficiency of the predetermined surface treatment application 14a. The portable wand system 10 also verifies and validates that the predetermined surface treatment application 14a is sufficient, correct, and complete. As used herein, "predetermined" means a target amount, or a desired amount, of surface treatment application to provide sufficient and effective coverage of one or more surfaces.

Now referring to FIG. 1B, FIG. 1B shows exemplary versions of surfaces 12, surface treatment applications 14, and surface treatment application elements (STAE) 16 used with exemplary versions of the portable wand system 10 (see FIG. 1A) of the disclosure.

As shown in FIG. 1B, the one or more surfaces 12 to be surface treated preferably comprise one or more interior surfaces 12a, in an interior 146 of one of, an aircraft 148, a spacecraft 150, an automotive vehicle 152, a watercraft 154, a train 156, a hospital 158, a factory building 160, an office building 162, a movie theater 164, a restaurant 166, or another suitable interior surface. When the user 52 of the portable wand system 10 presses the user input button 24 (see FIG. 1A), the one or more registration features 130 (see FIG. 1A) identify a starting position 167 (see FIG. 1B) at one of the one or more surfaces 12 to be surface treated.

As further shown in FIG. 1B, the surface treatment application 14, such as the predetermined surface treatment application 14a, comprises one of, a disinfection operation 168, an ultraviolet (UV) light disinfection operation 170 for an ultraviolet (UV) light disinfection 172, a decontamination operation 174, a sanitization operation 176, a sterilization operation 178, a curing operation 180, a shot peening operation 182, a chemical contaminant detection operation 184, a biological contaminant detection operation 186, a non-destructive inspection process 188, an eddy current crack detection 190, a paint application 192, an abrasive media blasting operation 194, a sand blasting operation 194a, a surface pre-heating operation 196, a torch welding operation 198, or another suitable surface treatment application. Preferably the surface treatment application 14 (see FIG. 1B) is a predetermined surface treatment application 14 (see FIG. 1B) that is predetermined by amount and coverage.

Preferably, the UV light disinfection 172 is a predetermined ultraviolet (UV) light disinfection 172a (see FIG. 1B) that is predetermined by amount and coverage. For a predetermined UV light disinfection 172a, the level of treatment is preferably in a range of 2 (two) millijoules per square centimeter to 100 (one hundred) millijoules per square centimeter irradiance of UV light 28. Preferably, the traversing speed of the wand applicator 18 across the surface 12 to be disinfected, or surface treated, for the predetermined UV light disinfection 172 is in a range of 1 (one) inch per second to 10 (ten) inches per second. Preferably, the distance the wand applicator 18 is held by the user 52 from the surface 12 to be disinfected or surface treated is in a range of 1 (one) inch to 6 (six) inches.

As further shown in FIG. 1B, the surface treatment application element 16 comprises one of, an ultraviolet (UV) lamp element 26, a gaseous dispersal element 200, an aerosolized element 202, a disinfectant fluid 204, a disinfectant gas 206, a sanitizing fluid 208, a sanitizing gas 210, a sterilizing fluid 212, a sterilizing gas 214, a cleaning solution 216, a curing element 218, a shot peening element 220, a contamination detection element 222, a paint 224, an abrasive media blasting element 226, a sand blasting element 226a, a surface pre-heating element 228, and a torch welding element 230.

Figure 2A:
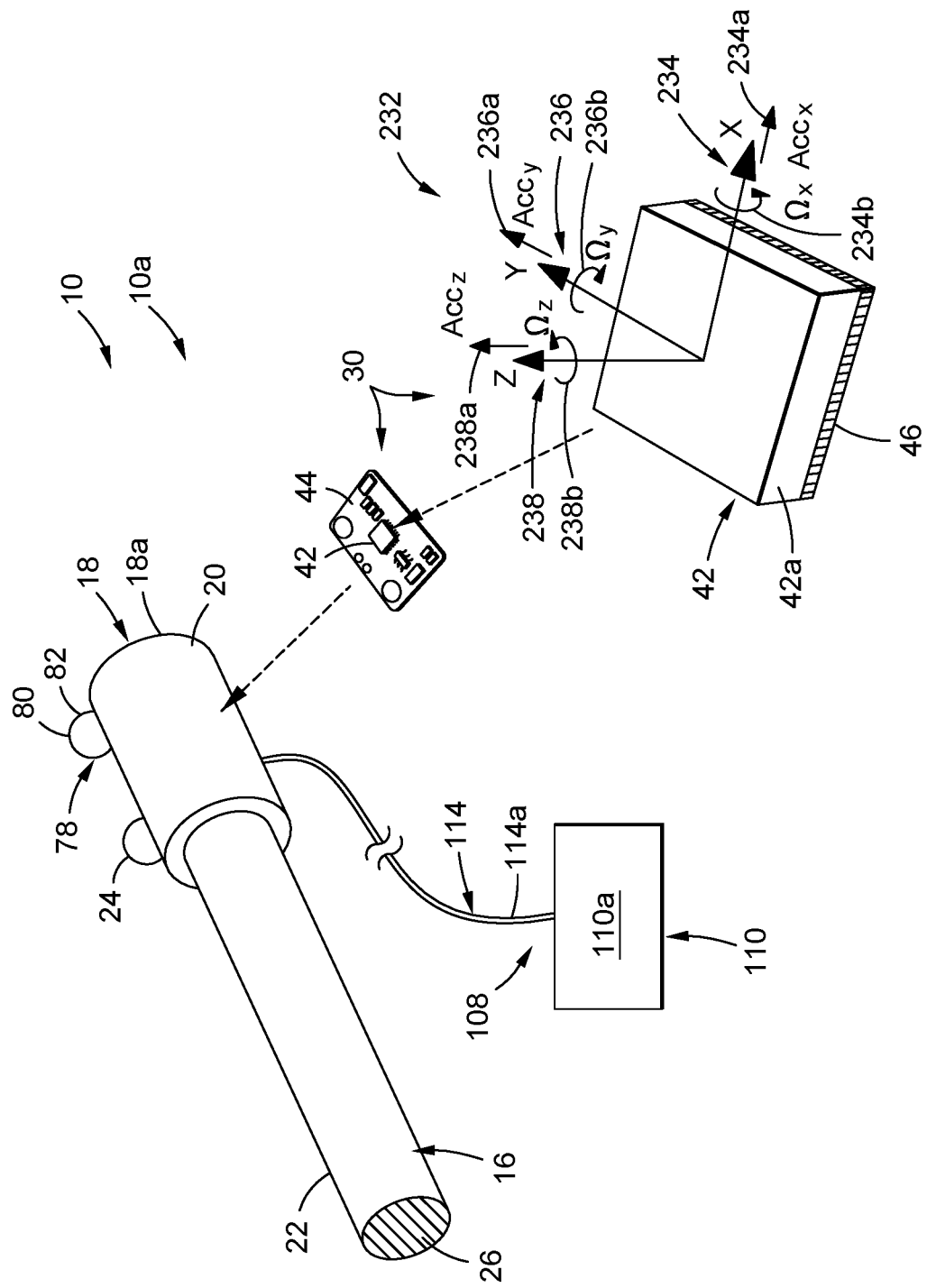
FIG. 2A is an illustration of a perspective view of a version of a portable wand system of the disclosure with a binary indicator.
Figure 2B:
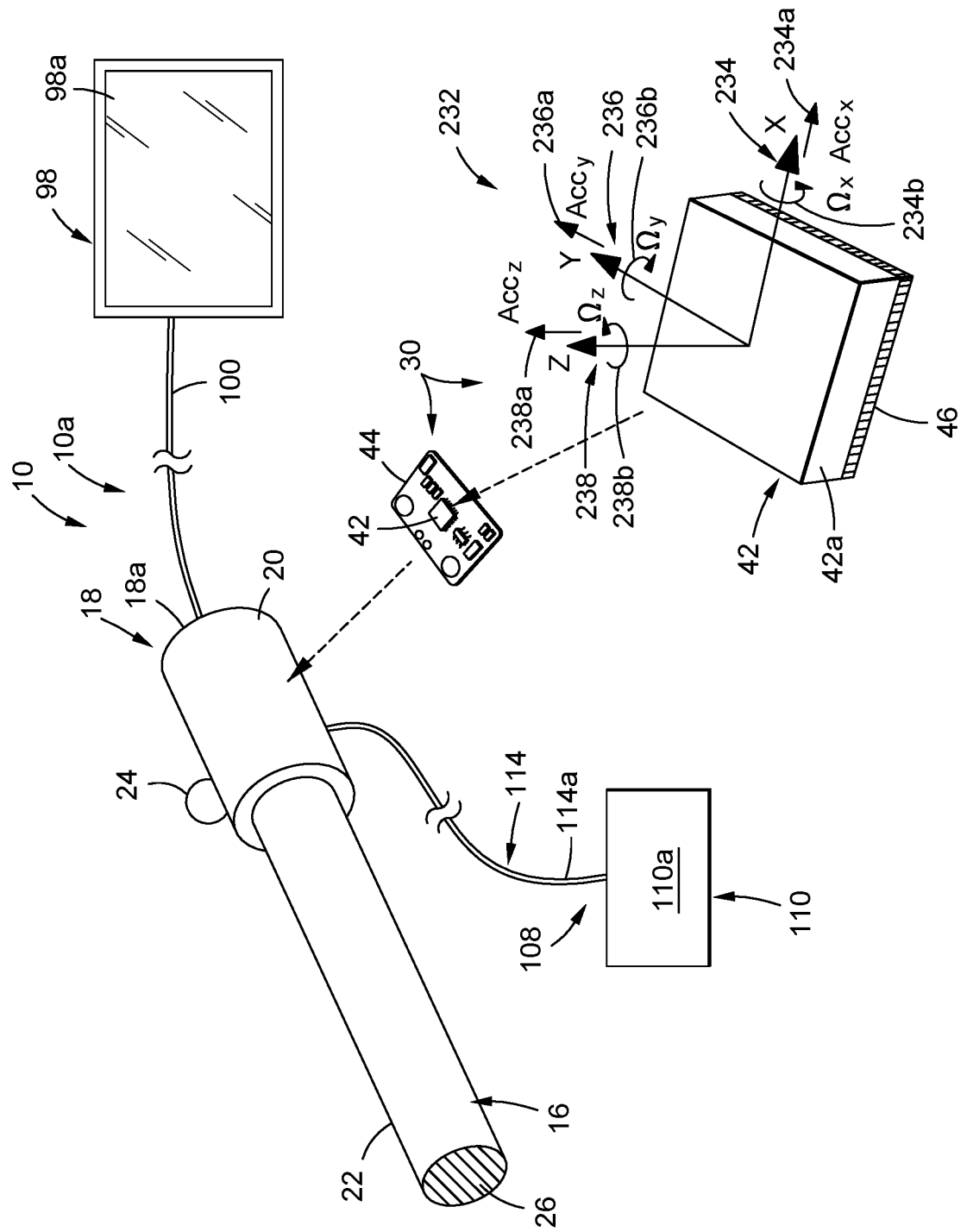
FIG. 2B is an illustration of a perspective view of the portable wand system of FIG. 2A with a video display.

Now referring to FIGS. 2A-2B, FIG. 2A is an illustration of a perspective view of a version of a portable wand system 10, such as the portable wand system 10a, of the disclosure, with an indicator element 78 in the form of a binary indicator 80. FIG. 2B is an illustration of a perspective view of the portable wand system 10, such as portable wand system 10a, of FIG. 2A, with an indicator element 78 in the form of a video display 98.

As shown in FIGS. 2A-2B, the portable wand system 10, such as portable wand system 10a, comprises the wand applicator 18, such as the handheld wand applicator 18a, having the handle portion 20 and the head portion 22. The head portion 22 contains the surface treatment application element 16, in the form of the ultraviolet (UV) lamp element 26.

As further shown in FIGS. 2A-2B, the portable wand system 10, such as the portable wand system 10a, comprises the user input button 24 on the handle portion 20. In FIG. 2A, the indicator element 78 is on the handle portion 20 and comprises the binary indicator 80, such as a light signal 82. However, the binary indicator 80 may comprise another type of binary indicator as shown in FIG. 1A.

In FIG. 2B, the indicator element 78 is connected to the handle portion 20, via a connector element 100, and comprises a video display 98, such as a video progress display 98a, to show the progress of the surface treatment application 14 (see FIG. 1B), such as UV light disinfection 172 (see FIG. 1B), on the one or more surfaces 12 (see FIG. 1B) to be surface treated, such as disinfected, sanitized, sterilized, or another type of surface treatment.

As further shown in FIGS. 2A-2B, the portable wand system 10, such as the portable wand system 10a, comprises the power assembly 108 comprising the energy storage device 110, such as a battery 110*a*. The energy storage device 110 is connected to the wand applicator 18, via a wired connector 114, such as a power interconnect cable 114*a*.

As further shown in FIGS. 2A-2B, the portable wand system 10, such as the portable wand system 10*a*, comprises the wand controller subsystem 30. In this version, the wand controller subsystem 30 is incorporated in the handle portion 20 of the wand applicator 18. In other versions, the wand controller subsystem 30 may be separate, but wired or wirelessly connected, to the wand applicator 18. For example, the wand controller subsystem 30 may be located in the system case 122 (see FIG. 1A), the system backpack 124 (see FIG. 1A), the system roller bag 126 (see FIG. 1A), the system shoulder case 128 (see FIG. 1A), or another transport or carrier apparatus, used to transport and store the portable wand system 10.

As further shown in FIGS. 2A-2B, the wand controller subsystem 30 comprises the inertial measurement unit (IMU) 42, such as the 6 degrees of freedom (DOF) inertial measurement unit 42*a*. The inertial measurement unit 42 comprises an integrated circuit 44 (see FIGS. 2A-2B) and comprises an accelerometer 46 (see FIGS. 2A-2B).

As further shown in FIGS. 2A-2B, the inertial measurement unit 42 uses an xyz coordinate axis system 232 to measure acceleration 48 (see FIG. 1A) and positions 50 (see FIG. 1A) of the wand applicator 18. FIGS. 2A-2B show an x-axis 234 with an x-acceleration 234*a* and an x-rotation 234*b*. FIGS. 2A-2B show a y-axis 236 with a y-acceleration 236*a* and a y-rotation 236*b*. FIGS. 2A-2B show a z-axis 238 with a z-acceleration 238*a* and a z-rotation 238*b*.

As shown in FIGS. 2A-2B, in another version of the disclosure, there is provided the portable wand system 10, such as the portable wand system 10*a*, for disinfecting one or more surfaces 12 (see FIG. 1B). Preferably, the surfaces 12 are in an interior 146 (see FIG. 1B) of an aircraft 148 (see FIG. 1B). However, the surfaces 12 may be in the interior 146 of other vehicles and structures, such as shown in FIG. 1B. The portable wand system 10, such as the portable wand system 10*a*, comprises the wand applicator 18 (see FIGS. 2A-2B) containing an ultraviolet (UV) lamp element 26 (see FIGS. 2A-2B). The UV lamp element 26 is operable to, or configured to, emit an ultraviolet (UV) light 28 (see FIG. 1A) preferably having a wavelength in a range between 200 nanometers to 280 nanometers, to disinfect the one or more surfaces 12. More preferably, the UV lamp element 26 comprises a 222 nm (nanometer) ultraviolet (UV) lamp element 26*a* (see FIG. 1A) operable to, or configured to, emit the UV light 28 having a wavelength of 222 nanometers.

As shown in FIGS. 2A-2B, the portable wand system 10 further comprises the user input button 24 coupled to the wand applicator 18. As shown in FIGS. 2A-2B, the portable wand system 10 further comprises the indicator element 78.

In one version, shown in FIG. 2A, the indicator element 78 comprises the binary indicator 80, such as in the form of a light signal 82 coupled to the wand applicator 18. The binary indicator 80 may further comprise, as shown in FIG. 1A, one of, a surface treatment application element (STAE) flashing light alert 84, for example, an ultraviolet (UV) lamp element flashing light alert 84*a*, an audio alert 86, a sound alert 88, a tactile alert 90, a vibration alert 92, a pulsing alert 94, a pressure altering alert 96, or another suitable binary indicator to indicate a predetermined UV light disinfection 172*a* (see FIG. 1B) of one or more of the one or more surfaces 12 is complete.

In another version, shown in FIG. 2B, the indicator element 78 comprises the video display 98, such as the video progress display 98*a*. The video display 98 is coupled to the wand applicator 18, via the connector element 100, such as an interconnect cable or power cord. The video display 98 is visible to the user 52 and shows one or more of, portions 102 (see FIG. 1A) of the one or more surfaces 12 to be disinfected, and a color coded signal 104 (see FIG. 1A), comprising a lighted progress bar 106 (see FIG. 1A), to indicate which portions have complete coverage, that is, to indicate complete coverage portions 102*a* (see FIG. 1A).

As shown in FIGS. 2A-2B, the portable wand system 10 further comprises the wand controller subsystem 30 coupled to the wand applicator 18. The wand controller subsystem 30 comprises a computer program 32 (see FIG. 1A), such as an algorithm 32*a* (see FIG. 1A), and a depiction 34 (see FIG. 1A) of one or more surfaces 12 to be disinfected with the UV lamp element 26. In one version, as shown in FIGS. 2A-2B, the wand controller subsystem 30 comprises the inertial measurement unit (IMU) 42, such as the 6 degrees of freedom inertial measurement unit (IMU) 42*a*. Alternatively to the IMU 42, the wand controller subsystem 30 may comprise separately, or in combination, one or more of, a fixed position extensometer 72, a rotary position sensor 74, and/or an external photogrammetric sensor 76.

As discussed above, the wand controller subsystem 30 further comprises a central processing unit (CPU) 60 (see FIG. 1A) coupled to the IMU 42, an ultraviolet (UV) lamp element power feedback 64 to the CPU 60, and a memory unit 66 coupled to the CPU 60. The wand controller subsystem 30 may further comprise a wireless network interface 70 coupled to the CPU 60.

As shown in FIGS. 2A-2B, the portable wand system 10 further comprises the power assembly 108, such as coupled to the wand applicator 18. As shown in FIGS. 2A-2B, the power assembly 108 comprises the energy storage device 110, such as the battery 110*a*. The energy storage device 110 is connected to the wand applicator 18, via the wired connector 114, such as the power interconnect cable 114*a*.

The portable wand system 10, such as the portable wand system 10*a*, further comprises one or more registration features 130 to register the wand applicator 18 against one or more known locations 132 (see FIG. 1A) at the one or more surfaces 12 in the depiction 34, for example, the geometric model 36, of the area or object with the one or more surfaces 12.

The portable wand system 10, such as the portable wand system 10*a*, measures positional data 58 (see FIG. 1A) of the wand applicator 18 in real-time, and compares the positional data 58 against the depiction 34, to indicate to a user 52 when a predetermined ultraviolet (UV) light disinfection 172*a* (see FIG. 1B) is achieved for the one or more surfaces 12.

The portable wand system 10 may further comprise the computer recording system 136 (see FIG. 1A) coupled to the wand controller subsystem 30. The computer recording system 136 is operable to, or configured to, analyze the positional data 58 of the wand applicator 18, and is operable to, or configured to, communicate to the indicator element 78 a status 173 (see FIG. 1B) of the UV light disinfection 172 (see FIG. 1B), such as the predetermined UV light disinfection 172*a*, of the one or more surfaces 12 with the UV lamp element 26.

Figure 3A:
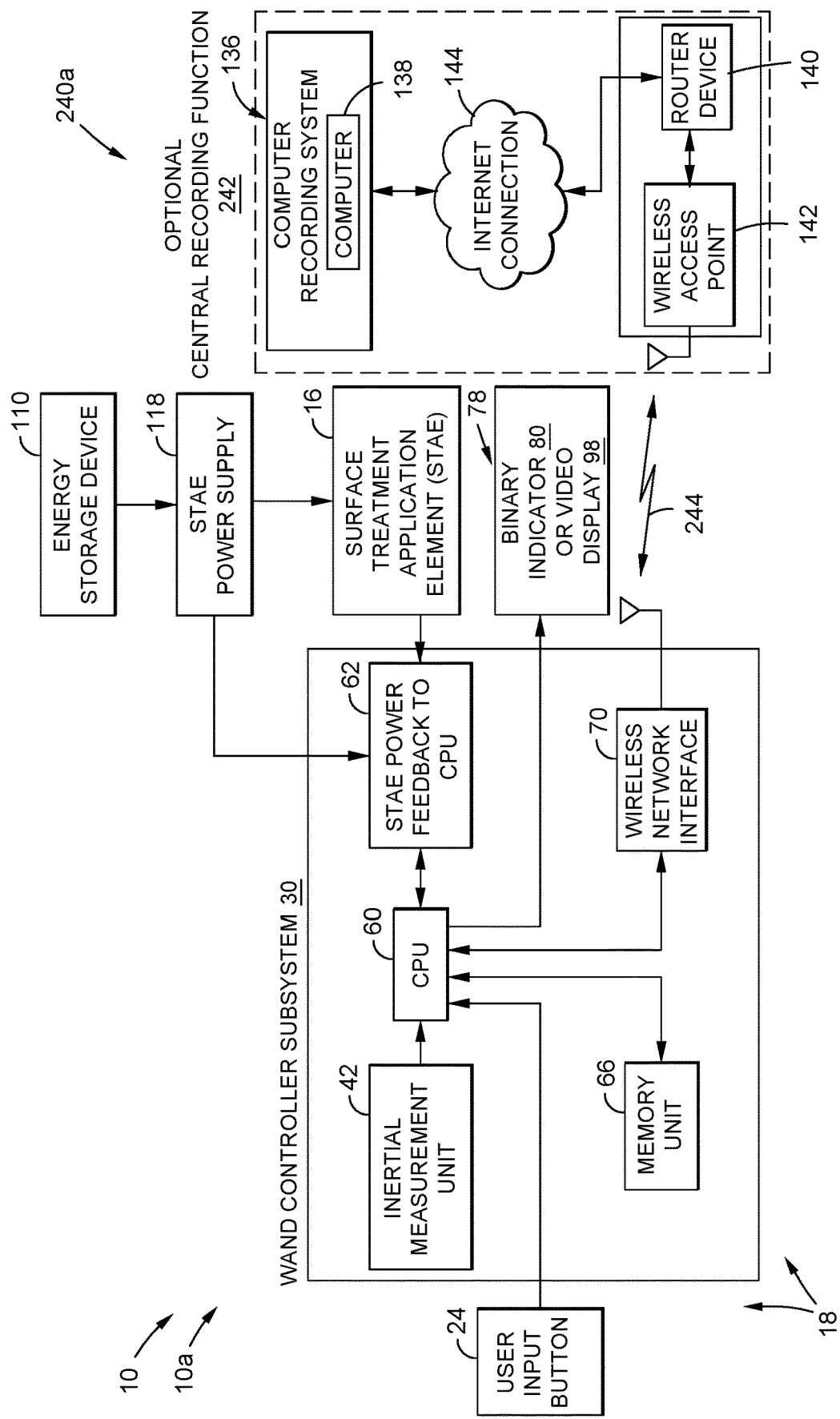
FIG. 3A is an illustration of a system flow diagram of a version of a portable wand system of the disclosure having a surface treatment application element and a computer recording system.
Figure 3B:
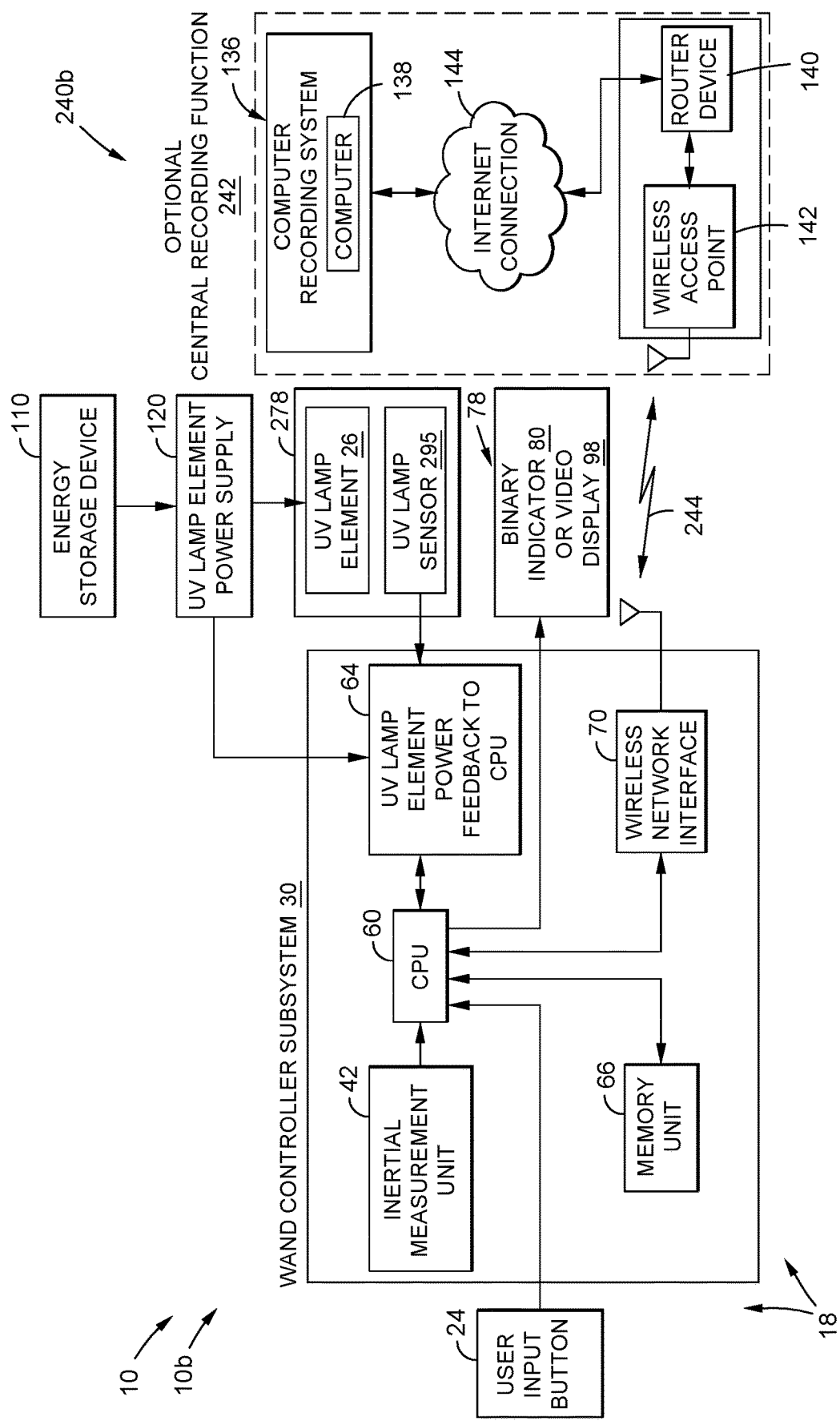
FIG. 3B is an illustration of a system flow diagram of a version of a portable wand system of the disclosure having an ultraviolet (UV) lamp element and a computer recording system.

Now referring to FIGS. 3A-3B, FIG. 3A is an illustration of a system flow diagram 240*a* of a version of a portable wand system 10, such as in the form of portable wand system 10*b*, of the disclosure, having a surface treatment application element 16 and a computer recording system 136. FIG. 3B is an illustration of a system flow diagram 240b of a portable wand system 10, such as in the form of portable wand system 10b, having an ultraviolet (UV) lamp element 26 and a computer recording system 136.

As shown in FIGS. 3A-3B, the portable wand system 10, such as in the form of portable wand system 10b, comprises the wand applicator 18 having the user input button 24, the wand controller subsystem 30, the energy storage device 110, the indicator element 78, and the computer recording system 136, which is optional. As shown in FIGS. 3A-3B, the user input button 24 and the inertial measurement unit (IMU) 42 are connected in a one-way communication to the CPU 60 of the wand controller subsystem 30. The IMU 42 measures the acceleration 48 (see FIG. 1A) and position 50 (see FIG. 1A) of the wand applicator 18 and sends the data 68 (see FIG. 1A) to the CPU 60.

As further shown in FIGS. 3A-3B, the memory unit 66 and the wireless network interface 70 are connected to the CPU 60 in a two-way communication. The memory unit 66 stores data 68 (see FIG. 1A). The CPU 60 can both store data 68 (see FIG. 1A) in the memory unit 66 and read data 68 from the memory unit 66. The CPU 60 can both send signals to the wireless network interface 70 and receive signals from the wireless network interface 70. As further shown in FIGS. 3A-3B, the CPU 60 sends data 68 to the indicator element 78, such as the binary indicator 80 or the video display 98.

As shown in FIG. 3A, the energy storage device 110 provides energy to a surface treatment application element (STAE) power supply 118, and the energy storage device 110 provides energy to a surface treatment application element (STAE) power feedback 62 to the CPU 60. As further shown in FIG. 3A, the surface treatment application element (STAE) power supply 118 supplies power to the surface treatment application element (STAE) 16, and the STAE 16 provides feedback to the STAE power feedback 62 to the CPU 60. The STAE power feedback 62 determines the surface treatment application element (STAE) 16 output and duration and sends the data 68 to the CPU 60.

As shown in FIG. 3B, the energy storage device 110 provides energy to a UV lamp element power supply 120 and provides energy to a UV lamp element power feedback 64 to the CPU 60. As further shown in FIG. 3B, the UV lamp element power supply 120 supplies power to a housing 278 that houses the UV lamp element 26 and an ultraviolet (UV) lamp sensor 295. The UV lamp sensor 295 may comprise a photosensor, for example, an ultraviolet (UV) fluence sensor, which is a photodiode device that measures the ultraviolet (UV) light output in real-time, and reports that value back as feedback to the UV lamp element power feedback 64 to the CPU 60. The UV lamp element power feedback 64 determines the UV lamp element 26 UV light output and duration and sends the data 68 to the CPU 60.

As further shown in FIGS. 3A-3B, the portable wand system 10, such as the portable wand system 10b, is wirelessly coupled to the computer recording system 136 to provide a central recording function 242, which is optional. The computer recording system 136 provides the central recording function 242 (see FIGS. 3A-3B) to document and record the complete coverage of the one or more surfaces 12 with the surface treatment application 14.

The computer recording system 136 comprises a computer 138 (see FIGS. 3A-3B). The CPU 60 converts the streams of data 68 (see FIG. 1A) and wirelessly transmits the position 50 (see FIG. 1A), based on a depiction 34, such as a geometric model 36, or a photographic image 38 taken with a photogrammetric process 40, and duration, to the computer recording system 136. The computer recording system 136 verifies location, and calculates position, and provides feedback, as to what surface 12, object, and/or area, still needs to be surface treated.

The computer 138 is wirelessly connected to a router device 140 (see FIGS. 3A-3B), via an internet connection 144 (see FIGS. 3A-3B). As shown in FIGS. 3A-3B, the router device 140 is connected to a wireless access point 142. As shown in FIGS. 3A-3B, the wireless network interface 70 is wirelessly connected, via a wireless connection 244, to the wireless access point 142 of the central recording function 242.

Figure 4:
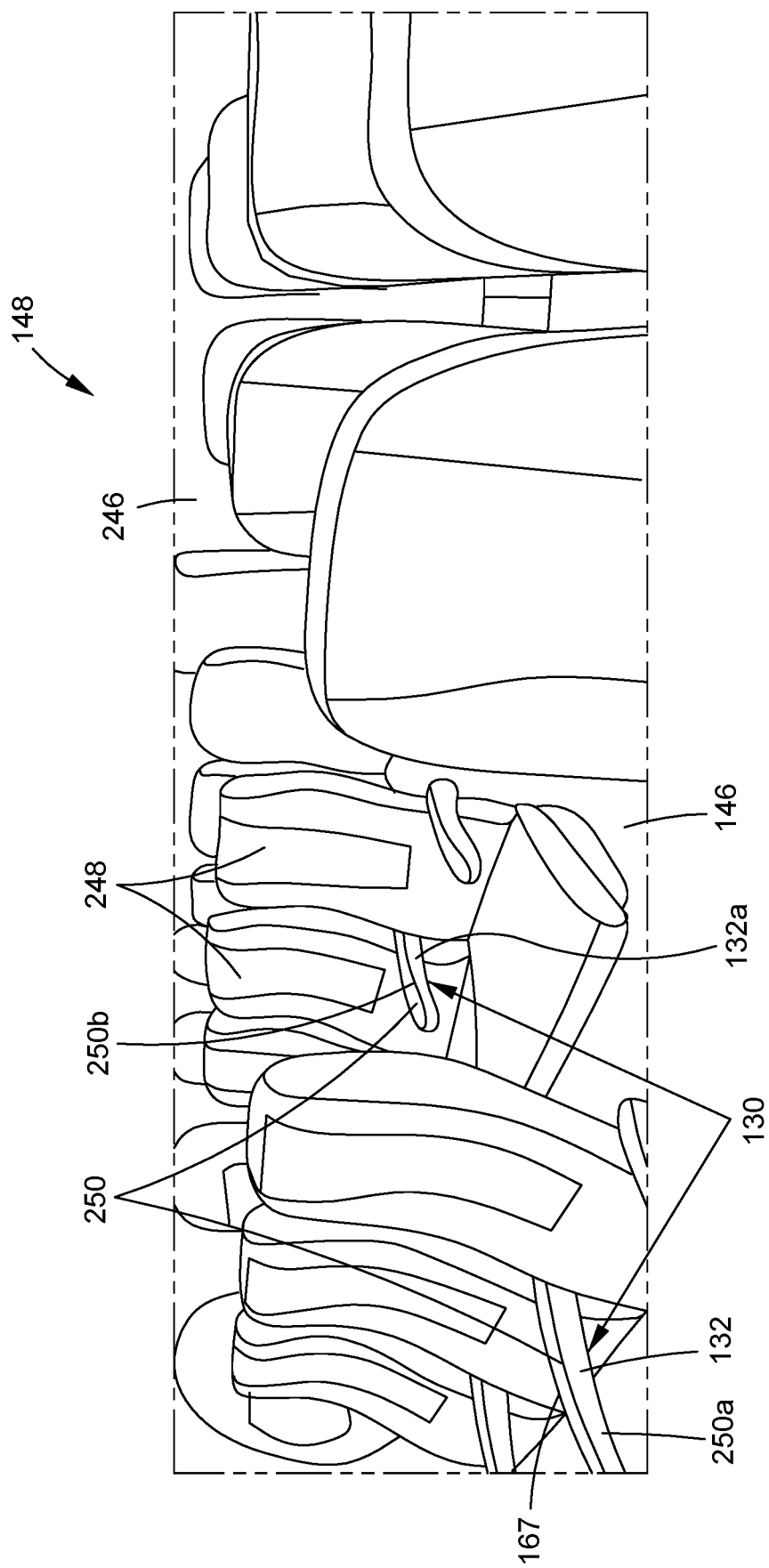
FIG. 4 is an illustration of a front perspective view of an interior of an aircraft showing registration features.

Now referring to FIG. 4, FIG. 4 is an illustration of a front perspective view of an interior 146 of a cabin 246 of an aircraft 148 showing seats 248 and registration features 130. In an exemplary version, the registration features 130 comprise arm rests 250 of the seats 248. The registration features 130 are known locations 132 in the area or areas to be treated with the surface treatment application 14, such as the predetermined surface treatment application 14a.

To enable use of an inertial measurement unit 42 with a low-cost accelerometer 46 having measurement drift characteristics that only permit short duration operation before location errors become large, the wand applicator 18 may be periodically "registered" against a known location 132 or datum (i.e. temporarily placed in a known orientation and location), such as the arm rest 250 on the next seat 248 in sequence. For example, in FIG. 4, a forward arm rest 250a may serve as a starting position 167 for the wand applicator 18 and a known location 132, and an aft arm rest 250b comprises a subsequent known location 132a. Once the wand applicator 18 is positioned on the aft arm rest 250b at the subsequent known location 132a in the sequence, the user 52, such as the operator 54, then briefly presses the user input button 24 (see FIGS. 2A-2B) on the wand applicator 18 that provides the portable wand system 10 an indication to begin the next segment of surface treatment application 14, for example, UV light disinfection 172 (see FIG. 1B), starting in the subsequent known location 132a, and long enough to treat the one or more surfaces 12 in the sub-area until the next registration with the registration feature 130 occurs.

Figure 5A:
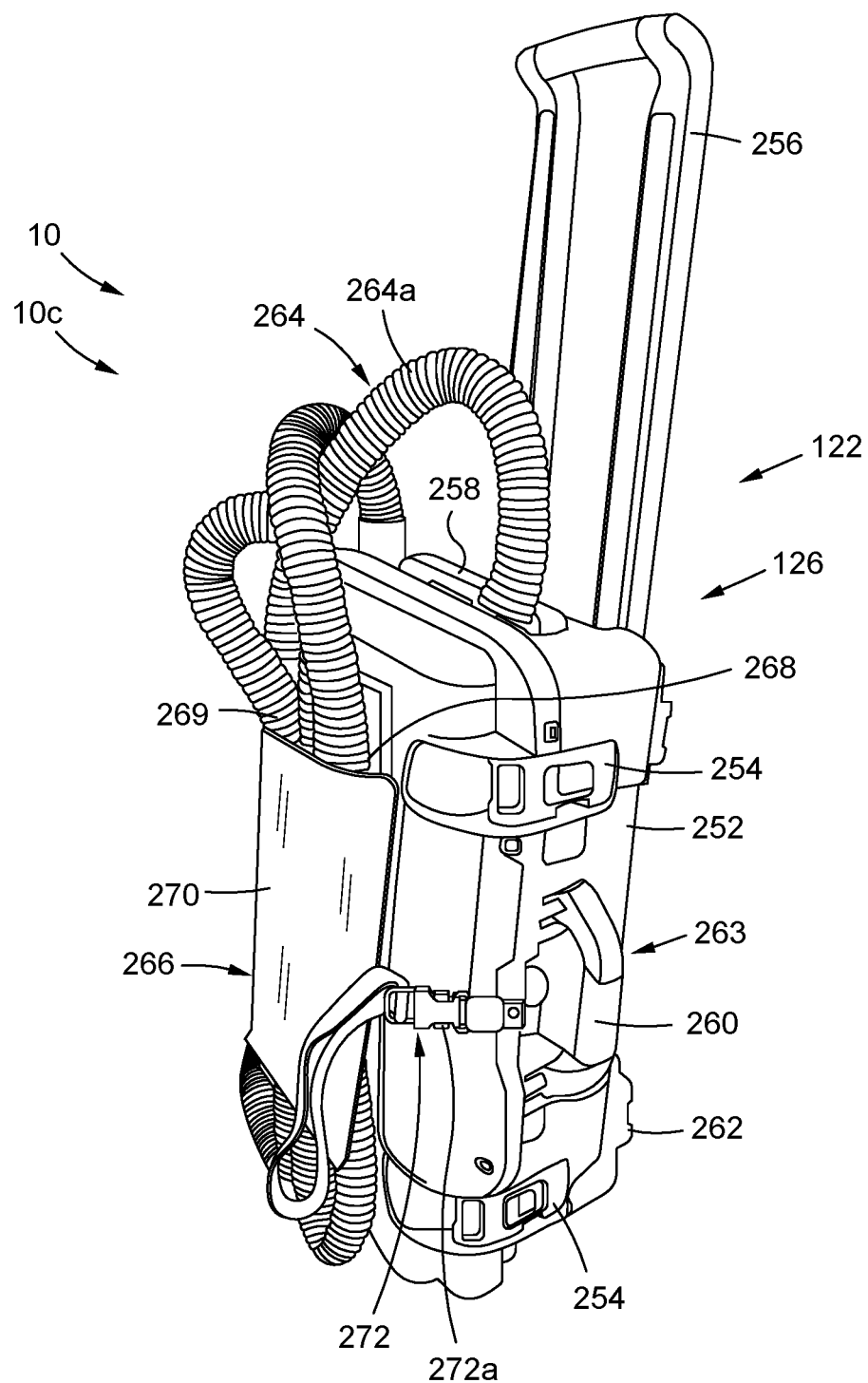
FIG. 5A is an illustration of a front perspective view of a portable wand system of the disclosure used with a system roller bag, where the system roller bag is in a closed position.

FIGS. 5A-5E show various views of a version of a portable wand system 10, such as in the form of portable wand system 10c, of the disclosure, used with a system case 122, such as in the form of a system roller bag 126. FIG. 5A is an illustration of a front perspective view of the portable wand system 10, such as the portable wand system 10c, used with the system case 122, such as the system roller bag 126, storing the wand applicator 18 (see FIG. 5B). FIG. 5A shows the system case 122, such as the system roller bag 126, having a hard shell case 252 with latches 254, a telescopic handle 256, a top handle 258, a side handle 260, and roller wheels 262. As shown in FIG. 5A, the system case 122, such as the system roller bag 126, is in a closed position 263. In this version, the portable wand system 10, such as the portable wand system 10c, further comprises a hose 264, such as an air hose 264a, that is attached to the wand applicator 18 (see FIG. 5B). As shown in FIG. 5A, the portable wand system 10, such as the portable wand system 10c, may further comprise a hose securing assembly 266 to secure the hose 264 against an outer surface 268 of the hard shell case 252. As shown in FIG. 5A, the hose securing assembly 266 comprises a fabric cover 270 coupled to a securing element 272, such as a buckle 272a, or other suitable securing element.

Figure 5B:
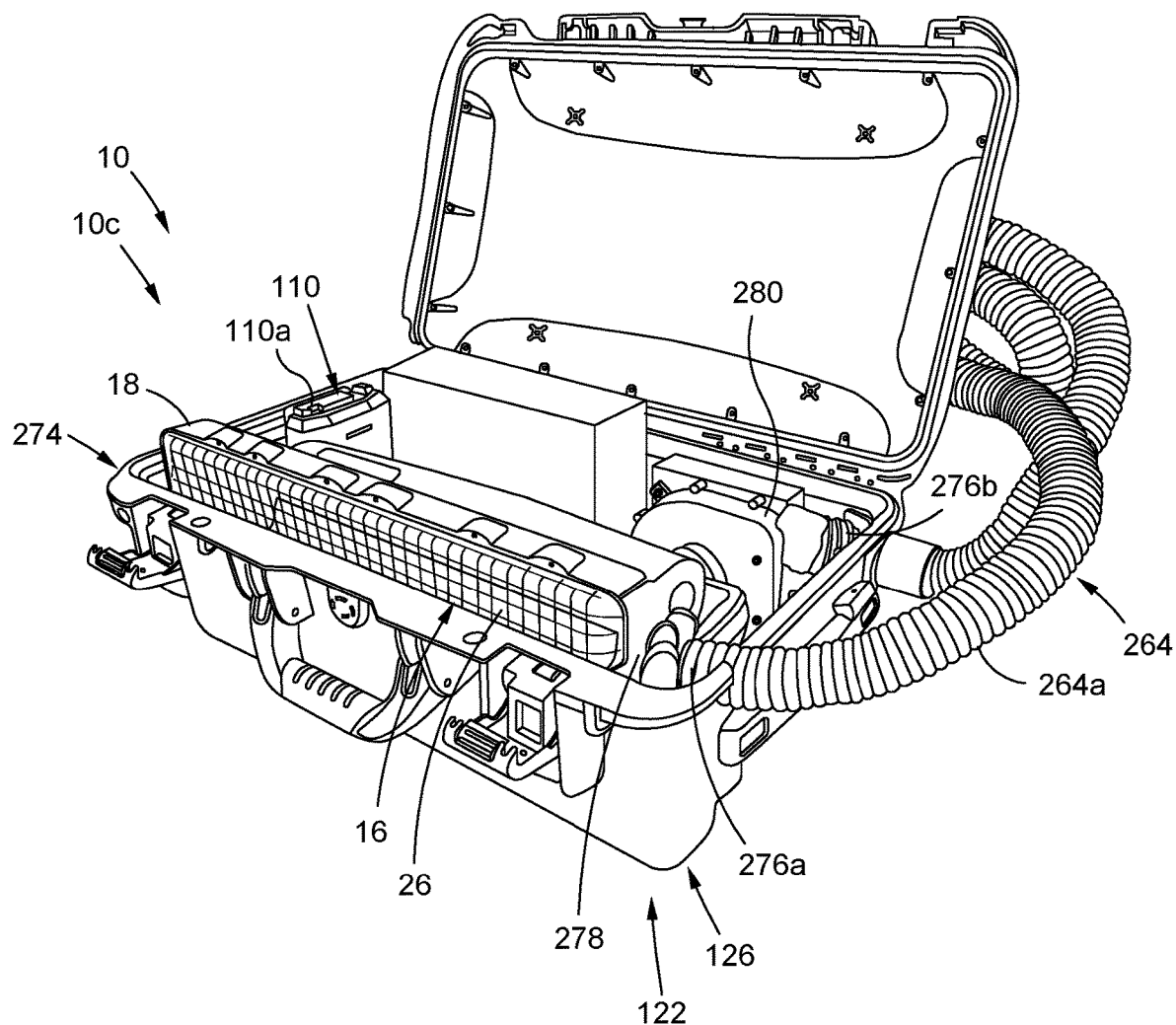
FIG. 5B is an illustration of a front side perspective view of the portable wand system of FIG. 5A used with the system roller bag, where the system roller bag is in an open position.

FIG. 5B is an illustration of a front side perspective view of the portable wand system 10, such as the portable wand system 10c, of FIG. 5A, used with the system case 122, such as the system roller bag 126, storing the wand applicator 18 and the energy storage device 110, such as a battery 110a. The system case 122, such as the system roller bag 126, is in an open position 274. The wand applicator 18 contains the surface treatment application element 16, such as in the form of the UV lamp element 26. FIG. 5B shows the hose 264, such as the air hose 264a, having a first end 276a attached to a housing 278 of the wand applicator 18, and having a second end 276b attached to a fan 280, such as a cooling fan. The fan 280 cools the wand applicator 18 containing the UV lamp element 26. The fan 280 also cools the energy storage device 110. In this version, the wand controller subsystem 30 (see FIG. 1A) is not in the handle portion 20 of the wand applicator 18, and is in a separate location inside the hard shell case 252 of the system roller bag 126.

Figure 5C:
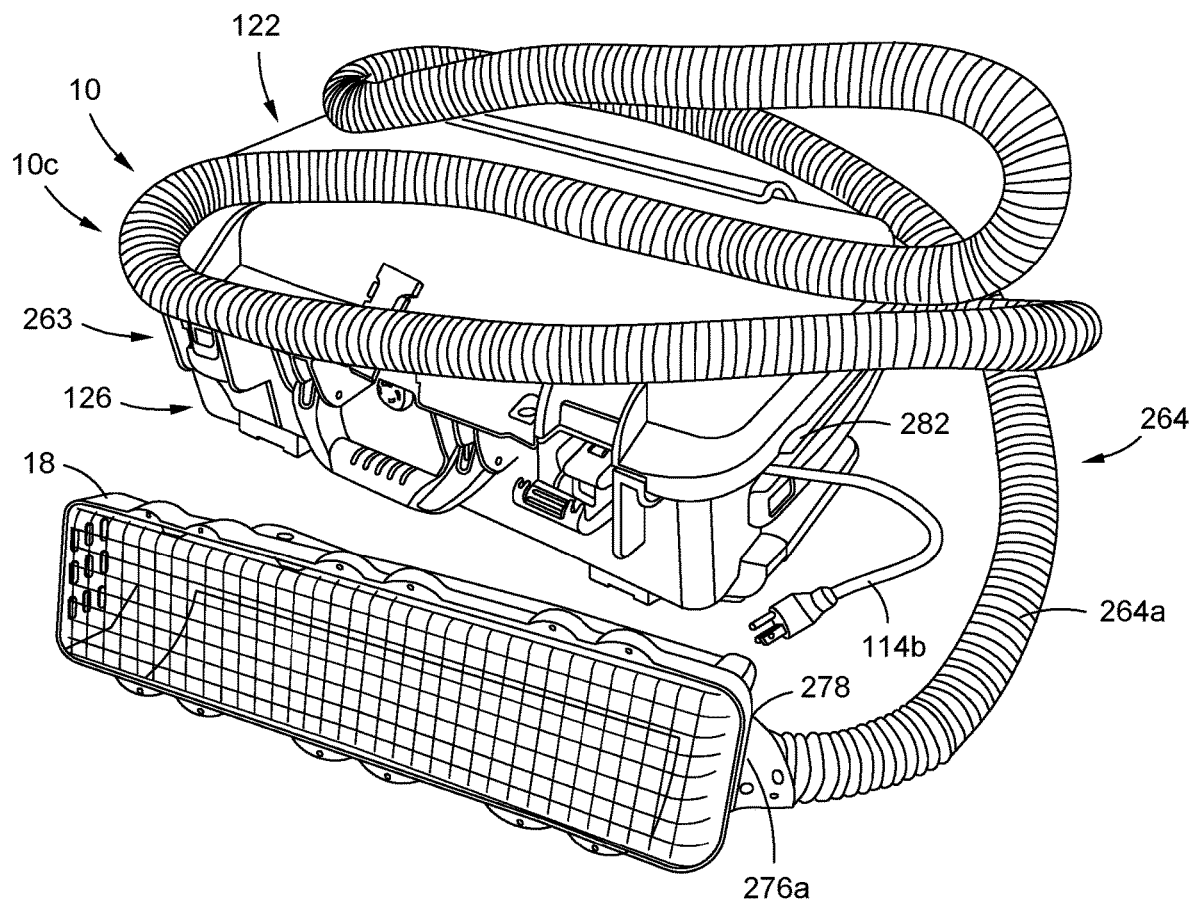
FIG. 5C is an illustration of a front side perspective view of the portable wand system 10 of FIG. 5B, with the system roller bag in the closed position.

FIG. 5C is an illustration of a front side perspective view of the portable wand system 10, such as the portable wand system 10c, of FIG. 5B, with the system case 122, such as the system roller bag 126, in the closed position 263, and the wand applicator 18 removed out of the system roller bag 126, ready for use by a user 52 (see FIG. 1A), such as an operator 54 (see FIG. 1A). FIG. 5C further shows a power cord 114b (see FIG. 5C) operable to, or configured to, be plugged into an outlet in an interior 146 (see FIG. 1B) of an aircraft 148 (see FIG. 1B), or another suitable vehicle or structure, to undergo a surface treatment application 14 with the portable wand system 10. The power cord 114b is stowed inside the system roller bag 126 during transit. The power cord 114b extends out of a notch opening 282 formed when the system roller bag 126 is in the closed position 263.

Figure 5D:
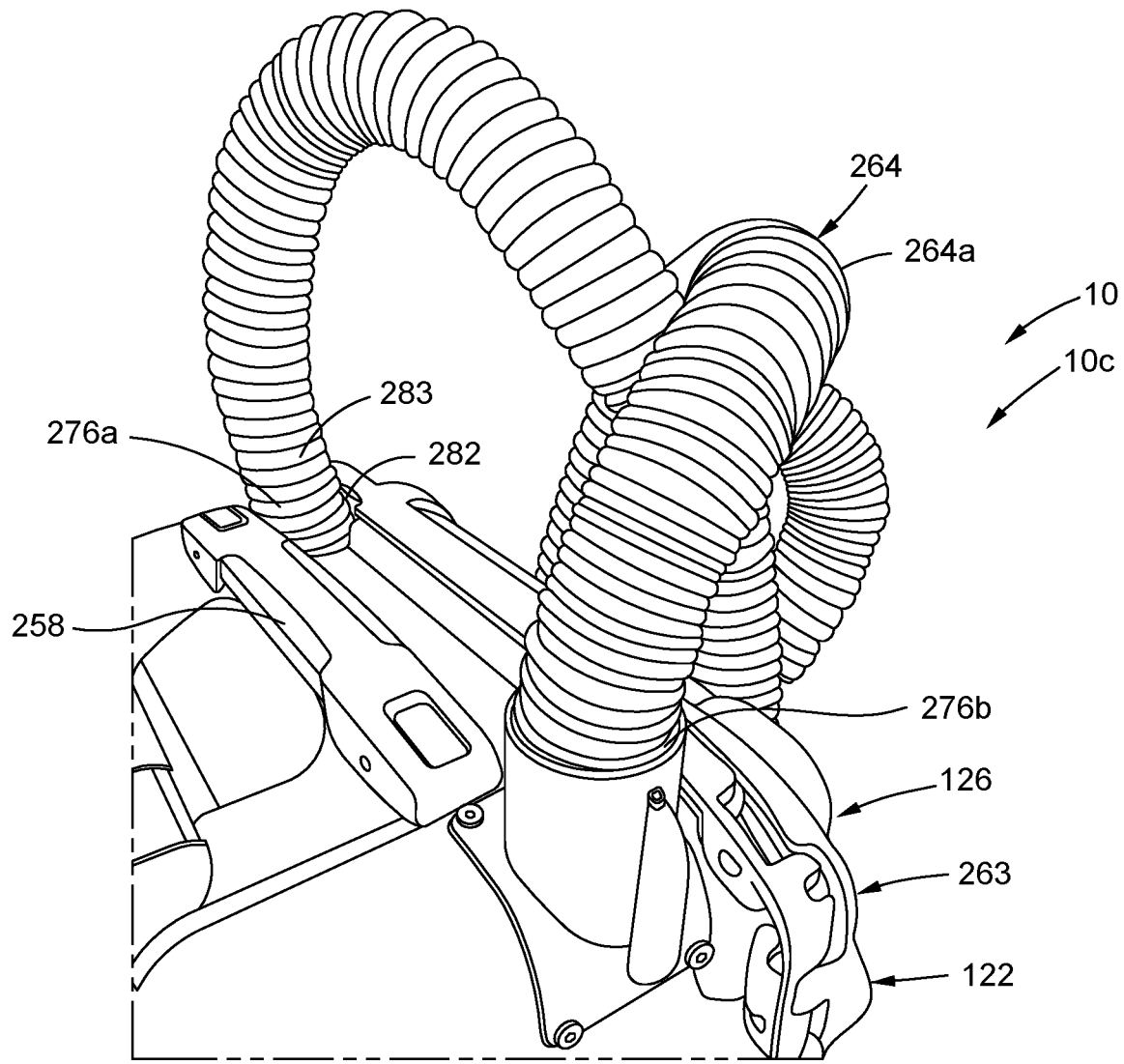
FIG. 5D is an illustration of an enlarged top end view of the system roller bag of FIG. 5A, and shows a hose of the portable wand system, and shows the system roller bag in the closed position.

FIG. 5D is an illustration of an enlarged top end view of the system case 122, such as the system roller bag 126, of FIG. 5A, and the hose 264, such as the air hose 264a, of the portable wand system 10, such as the portable wand system 10c. The system case 122, such as the system roller bag 126, is in the closed position 263. FIG. 5D shows the first end 276a of the hose 264 extending out of the notch opening 282. The hose 264 exits the system roller bag 126 during transit, when the system roller bag 126 is in the closed position 263. The notch opening 282 also allows intake air to be drawn into the fan 280 (see FIG. 5B) even when the system roller bag 126 is in the closed position 263 during operation.

Figure 5E:
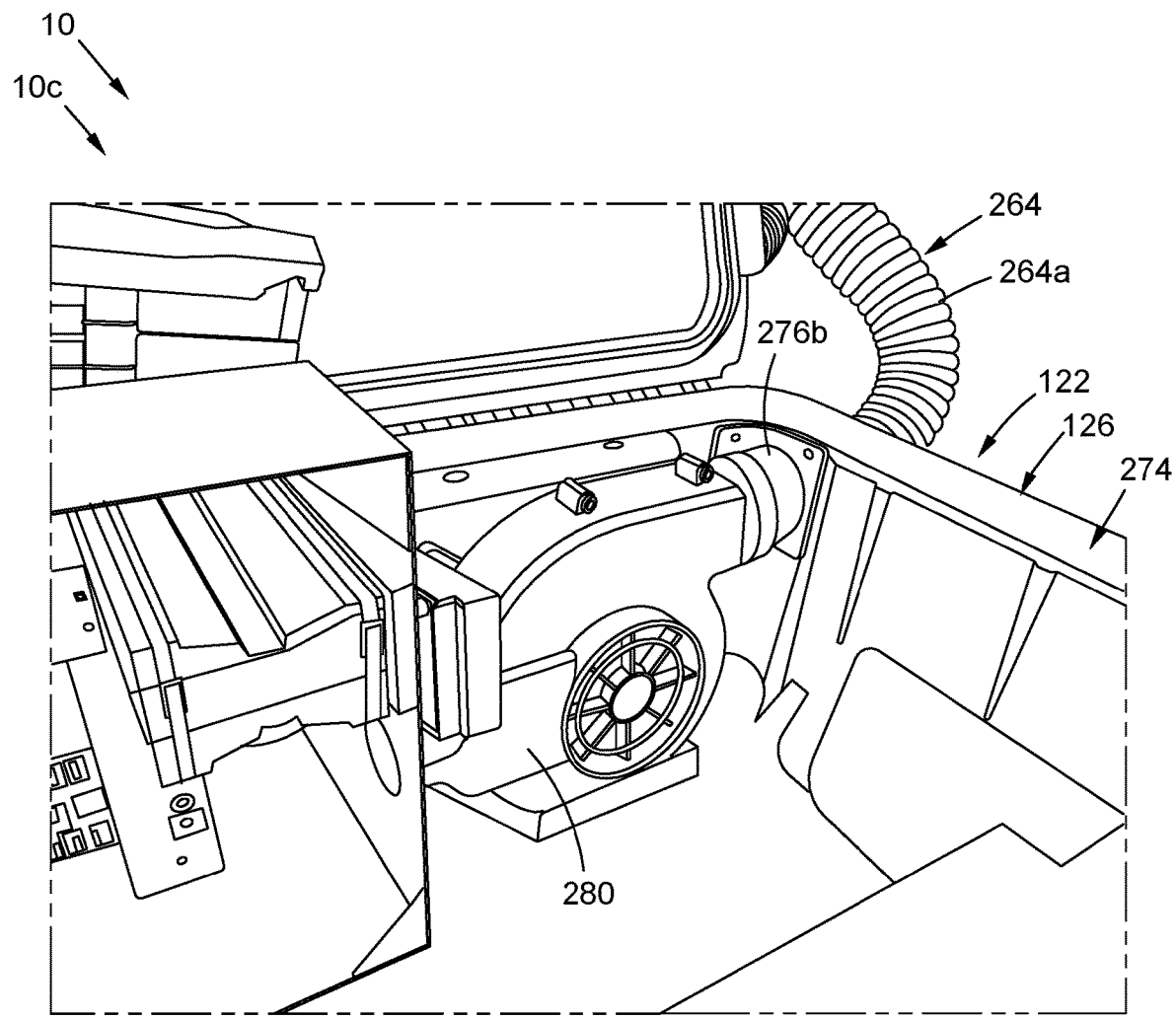
FIG. 5E is an illustration of an enlarged front perspective view of a fan of the portable wand system of FIG. 5B, with the system roller bag in the open position.

FIG. 5E is an illustration of an enlarged front perspective view of the fan 280 of the portable wand system 10, such as the portable wand system 10c, of FIG. 5B, with the system case 122, such as the system roller bag 126, in the open position 274. FIG. 5E further shows the second end 276b of the hose 264, such as the air hose 264a, attached to the fan 280.

Figure 6A:
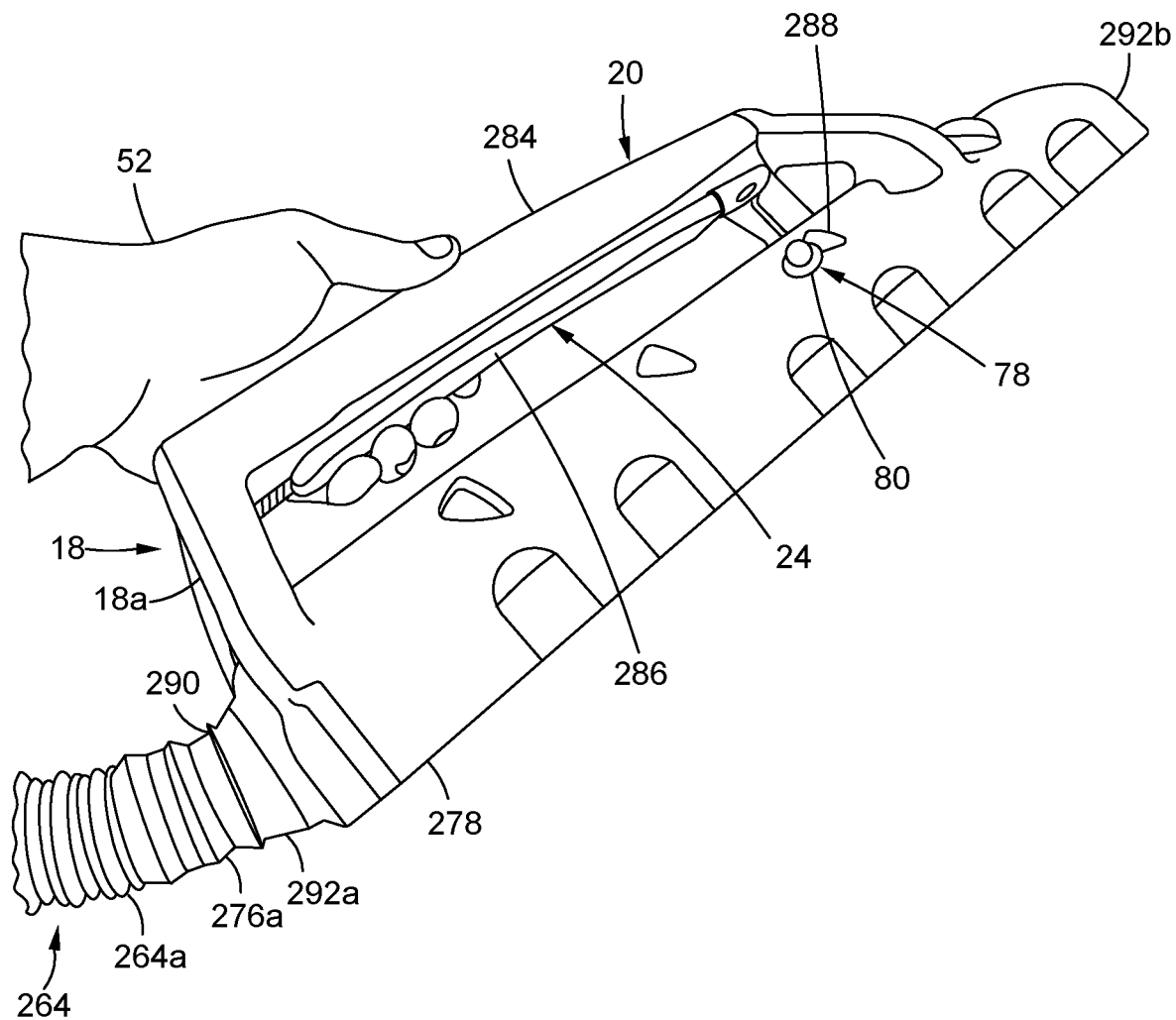
FIG. 6A is an illustration of a side perspective view of a version of a wand applicator held by a user.
Figure 6B:
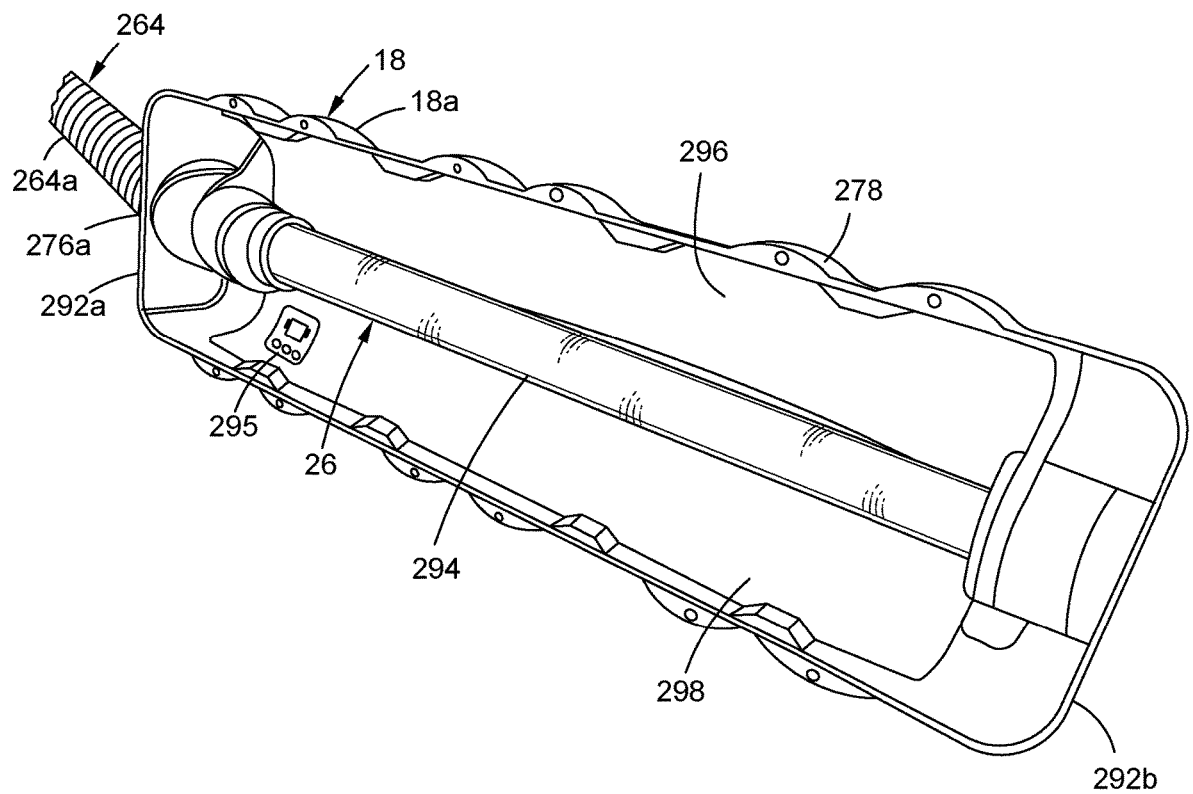
FIG. 6B is an illustration of a bottom perspective view of the wand applicator of FIG. 6A.
Figure 6C:
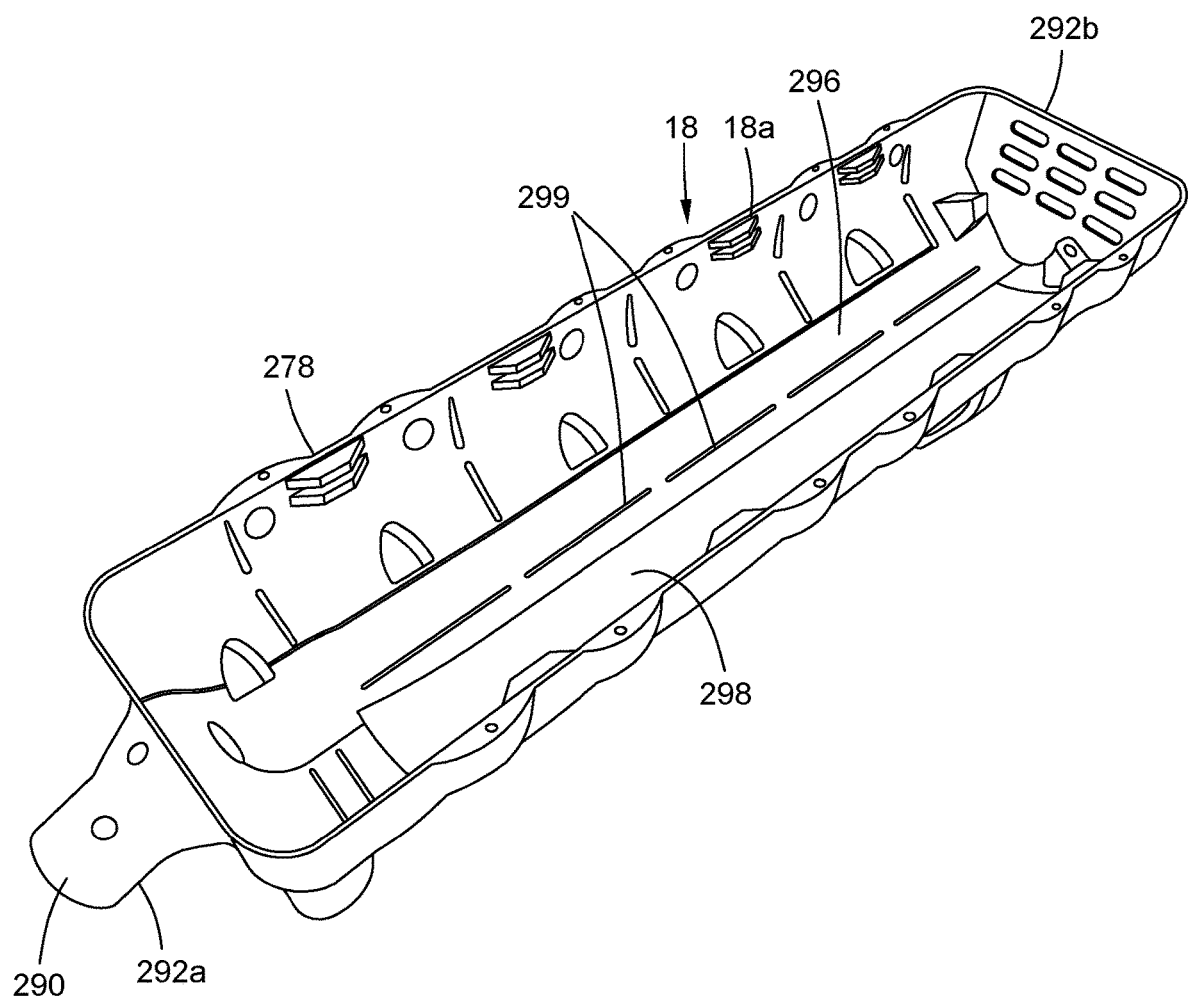
FIG. 6C is an illustration of a bottom perspective view of the wand applicator of FIG. 6B.

FIGS. 6A-6C show various views of a version of a wand applicator 18, such as handheld wand applicator 18a, for one or more versions of a portable wand system 10 (see FIGS. 1A, 2A-2B, 3A-3B), of the disclosure. FIG. 6A is an illustration of a side perspective view of a version of the wand applicator 18, such as the handheld wand applicator 18a, held by a user 52. As shown in FIG. 6A, the user 52 holds the handle portion 20 comprising a trigger handle 284. In this version, the user input button 24 comprises a trigger portion 286 that may be triggered or actuated by the user anywhere along the length of the trigger portion 286. FIG. 6A further shows the indicator element 78, such as in the form of the binary indicator 80, coupled to an exterior portion 288 of the housing 278. FIG. 6A further shows the first end 276a of the hose 264, such as the air hose 264a, inserted through a port opening 290 at a first end 292a of the wand applicator 18. FIG. 6A further shows a second end 292b of the wand applicator 18. In this version, the wand controller subsystem 30 (see FIG. 1A) is not in the handle portion 20 of the wand applicator 18, and is in a separate location from the wand applicator 18.

FIG. 6B is an illustration of a bottom perspective view of the wand applicator 18, such as the handheld wand applicator 18a, of FIG. 6A. FIG. 6B shows the housing 278, the first end 292a, and the second end 292b of the wand applicator 18. FIG. 6B further shows the first end 276a of the hose 264, such as the air hose 264a, extending from the first end 292a of the wand applicator 18. FIG. 6B further shows a UV lamp element 26 comprising an ultraviolet (UV) lamp bulb 294. FIG. 6B further shows an ultraviolet (UV) lamp sensor 295 coupled to an interior 296 of the housing 278 and positioned in range of an emission path of the UV lamp bulb 294. The housing 278 houses the UV lamp bulb 294 and the UV lamp sensor 295. The UV lamp sensor 295 may comprise a photosensor, for example, an ultraviolet (UV) fluence sensor, which is a photodiode device that measures the ultraviolet (UV) light output in real-time. As shown in FIG. 6B, the UV lamp bulb 294 is attached between the first end 292a and the second end 292b in the interior 296 of the housing 278. FIG. 6B further shows a reflector lining element 298 lining the interior 296 of the housing 278, and positioned behind the UV lamp element 26 comprising the UV lamp bulb 294.

FIG. 6C is an illustration of a bottom perspective view of the wand applicator 18, such as the handheld wand applicator 18a, of FIG. 6B. FIG. 6C shows the housing 278, the first end 292a, and the second end 292b of the wand applicator 18. FIG. 6B further shows the port opening 290. FIG. 6C further shows the UV lamp element 26 (see FIG. 6B) comprising the UV lamp bulb 294 (see FIG. 6B) removed and shows half of the reflector lining element 298 removed. FIG. 6C further shows a cooling manifold 299 in the interior 296 of the housing 278 and underneath the reflector lining element 298.

In another version of the disclosure, as shown in FIGS. 1A-1B, 5A-5E and 6A-6C, there is provided a portable wand system 10, such as portable wand system 10c, for performing a surface treatment application 14, such as a UV light disinfection operation 170 (see FIG. 1B), on one or more surfaces 12. The portable wand system 10, such as portable wand system 10c, comprises a system case 122 (see FIG. 1A). The system case 122 may comprise one of, a system backpack 124 (see FIG. 1A), a system roller bag (see FIG. 1A), a system shoulder case (see FIG. 1A), or another suitable case, carrier, or bag.

The portable wand system 10, such as portable wand system 10c, further comprises a wand applicator 18 comprising a housing 278 (see FIG. 6A) that houses an ultraviolet (UV) lamp element 26 (see FIG. 6A), such as an ultraviolet (UV) lamp bulb 294, and also houses an ultraviolet (UV) lamp sensor 295 (see FIG. 6B). The wand applicator 18 is attached to the system case 122, such as a system roller bag 126 (see FIG. 5A), via a hose 264 (see FIG. 5B), such as an air hose 264a (see FIG. 5B). The hose 264 has a first end 276a (see FIG. 5B) attached to the wand applicator 18, and has a second end 276b (see FIG. 5B) attached to a fan 280, such as a cooling fan, positioned in the system case 122, such as the system roller bag 126. The system case 122, such as the system roller bag 126, comprises a notch opening 282 (see FIG. 5D), to receive a portion 283 (see FIG. 5D) of the hose, and to allow the wand applicator 18 to be stowed in the system case 122, when the system case 122 is in a closed position 263 (see FIG. 5A). The system case 122, such as the system roller bag 126, may further comprise a hose securing assembly 266 (see FIG. 5A) attached to an outer surface 268 (see FIG. 5A) of the system case 122, to secure a portion 269 (see FIG. 5A) of the hose 264.

The housing 278 may further comprise a port opening 290 (see FIG. 6A) for receiving the first end 276a of the hose 264, and may further comprise a trigger handle 284 (see FIG. 6A). As shown in FIG. 6C, the housing 278 may further comprise a cooling manifold 299 in an interior 296 of the housing 278, and may further comprise a reflector lining element 298 positioned over the cooling manifold 299 in the interior 296 of the housing 278.

The portable wand system 10, such as portable wand system 10c, further comprises a wand controller subsystem 30 (see FIG. 1A) coupled to the wand applicator 18. The wand controller subsystem 30 is preferably positioned in the system case 122, such as the system roller bag 126. The wand controller subsystem 30 comprises a computer program 32 and a depiction 34 of one or more surfaces 12 to be surface treated, or disinfected, with the UV lamp element 26. The portable wand system 10, such as portable wand system 10c, further comprises a user input button 24 (see FIG. 1A) coupled to the wand applicator 18. The portable wand system 10, such as portable wand system 10c, further comprises an indicator element 78 (see FIG. 6A). The portable wand system 10, such as portable wand system 10c, further comprises a power assembly 108 (see FIG. 1A) coupled to the wand applicator 18, and positioned in the system case 122, such as the system roller bag 126.

The portable wand system 10, such as portable wand system 10c, further comprises one or more registration features 130 (see FIG. 1A) to register the wand applicator 18 against one or more known locations 132 (see FIG. 1A) on the one or more surfaces 12 in the depiction 34. The portable wand system 10 measures positional data 58 of the wand applicator 18 in real-time, and compares the positional data 58 against the depiction 34, to indicate to a user 52 when a predetermined surface treatment application 14a (see FIG. 1B) is achieved for the one or more surfaces 12.

The portable wand system 10, such as portable wand system 10c, may further comprise a computer recording system 136 (see FIG. 1A) coupled to the wand controller subsystem 30. The computer recording system 136 is operable to, or configured to, analyze the positional data 58 of the wand applicator 18, and is operable to, or configured to, communicate to the indicator element 78 a status 15 (see FIG. 1B) of the predetermined surface treatment application 14a of the one or more surfaces 12 with the UV lamp element 26.

Figure 7:
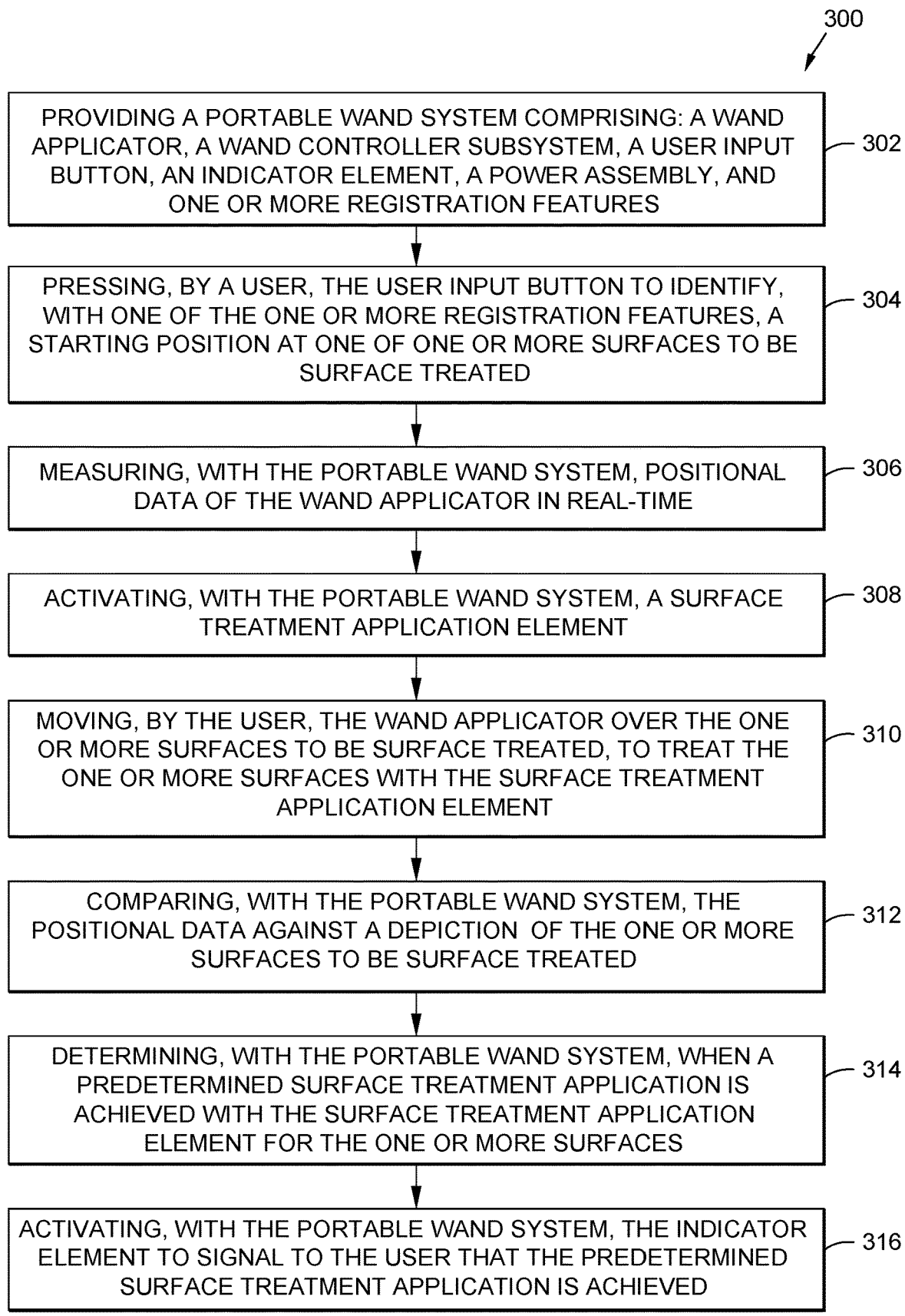
FIG. 7 is an illustration of a flow diagram of a version of a method of the disclosure.

Now referring to FIG. 7, FIG. 7 is an illustration of a flow diagram of a version of a method 300 of the disclosure. In another version of the disclosure, there is provided the method 300 for indicating to a user 52 (see FIG. 1A) when a predetermined surface treatment application 14a (see FIG. 1B) is achieved for one or more surfaces 12 (see FIGS. 1A-1B).

The blocks in FIG. 7 represent operations and/or portions thereof, or elements, and lines connecting the various blocks do not imply any particular order or dependency of the operations or portions thereof, or elements. FIG. 7 and the disclosure of the steps of the method 300 set forth herein should not be interpreted as necessarily determining a sequence in which the steps are to be performed. Rather, although one illustrative order is indicated, it is to be understood that the sequence of the steps may be modified when appropriate. Accordingly, certain operations may be performed in a different order or simultaneously.

As shown in FIG. 7, the method 300 comprises the step of providing 302 a version of a portable wand system 10 (see FIGS. 1A, 2A-2B, 3A-3B, 5). As discussed in detail above, in one version, the portable wand system 10 comprises a wand applicator 18 (see FIG. 1A) containing a surface treatment application element 16. The portable wand system 10 further comprises a wand controller subsystem 30 (see FIG. 1A) coupled to the wand applicator 18. The wand controller subsystem 30 comprises a computer program 32 (see FIG. 1A), such as an algorithm 32a (see FIG. 1A), and a depiction 34 (see FIG. 1A) of one or more surfaces 12 to be surface treated with a surface treatment application 14 (see FIG. 1B), such as the predetermined surface treatment application 14a, of the surface treatment application element 16. The portable wand system 10 further comprises a user input button 24 (see FIG. 1A) coupled to the wand applicator 18. The portable wand system 10 further comprises an indicator element 78 (see FIG. 1A).

The portable wand system 10 further comprises a power assembly 108 (see FIG. 1A) coupled to the wand applicator 18. The power assembly 108 may comprise an energy storage device 110, such as a battery 110a, coupled to the wand applicator 18, via a wired connector 114. The portable wand system 10 further comprises one or more registration features 130 (see FIG. 1A) to register the wand applicator 18 against one or more known locations 132 at the one or more surfaces 12 in the depiction 34, such as the geometric model 36 or photographic image 38.

The step of providing 302 the portable wand system 10 may further comprise, providing the portable wand system 10 comprising a computer recording system 136 (see FIG. 1A) coupled to the wand controller subsystem 30. The computer recording system 136 analyzes the positional data 58 of the wand applicator 18, and communicates to the indicator element 78 a status 15 (see FIG. 1B) of the surface treatment application 14 (see FIG. 1B), such as the predetermined surface treatment application 14a (see FIG. 1B), on the one or more surfaces 12. The computer recording system 136 comprises a computer 138 (see FIG. 1A) to record the surface treatment application 14, such as the predetermined surface treatment application 14a, of the one or more surfaces 12, to validate and verify that the surface treatment application 14, such as the predetermined surface treatment application 14a, of the one or more surfaces 12 is correct.

The step of providing 302 the portable wand system 10 may further comprise providing the portable wand system 10 comprising the wand controller subsystem 30 with the depiction 34 of the one or more surfaces 12 to be treated with the surface treatment application 14 comprising one of, a disinfection operation 168, an ultraviolet (UV) light disinfection operation 170, a decontamination operation 174, a sanitization operation 176, a sterilization operation 178, a curing operation 180, a shot peening operation 182, a chemical contaminant detection operation 184, a biological contaminant detection operation 186, a non-destructive inspection process 188, an eddy current crack detection 190, a paint application 192, an abrasive media blasting operation 194, a sand blasting operation 194a, a surface pre-heating operation 196, a torch welding operation 198, or another suitable surface treatment application.

The step of providing 302 the portable wand system 10 may further comprise providing the portable wand system 10 comprising the wand controller subsystem 30 with the depiction 34 comprising one of, a geometric model 36 of the one or more surfaces 12 to be surface treated with the surface treatment application 14 of the surface treatment application element 16, and a photographic image 38 (see FIG. 1A) obtained with a photogrammetric process 40 (see FIG. 1A).

As shown in FIG. 7, the method 300 further comprises the step of pressing 304, by the user 52, the user input button 24 to identify, with one of the one or more registration features 130, a starting position 167 (see FIG. 1B) at one of the one or more surfaces 12 to be surface treated.

As shown in FIG. 7, the method 300 further comprises the step of measuring 306, with the portable wand system 10, positional data 58 (see FIG. 1A) of the wand applicator 18 in real-time.

As shown in FIG. 7, the method 300 further comprises the step of activating 308, with the portable wand system 10, the surface treatment application element 16.

As shown in FIG. 7, the method 300 further comprises the step of moving 310, by the user 52, the wand applicator 18 over the one or more surfaces 12 to be surface treated, to treat the one or more surfaces 12 with the surface treatment application element 16.

The step of moving 310 the wand applicator 18 over the one or more surfaces 12 to be surface treated, to treat the one or more surfaces 12 with the surface treatment application element 16, may further comprise, moving the wand applicator 18 to treat the one or more surfaces 12 with the surface treatment application element 16 comprising, as shown in FIG. 1B, one of, an ultraviolet (UV) lamp element 26, a gaseous dispersal element 200, an aerosolized element 202, a disinfectant fluid 204, a disinfectant gas 206, a sanitizing fluid 208, a sanitizing gas 210, a sterilizing fluid 212, a sterilizing gas 214, a cleaning solution 216, a curing element 218, a shot peening element 220, a contamination detection element 222, a paint 224, an abrasive media blasting element 226, a sand blasting element 226a, a surface pre-heating element 228, a torch welding element 230, or another suitable surface treatment application element.

The step of moving 310 the wand applicator 18 over the one or more surfaces 12 to be surface treated may further comprise, moving the wand applicator 18 over the one or more surfaces 12 to be surface treated comprising one or more surfaces 12 in an interior 146, as shown in FIG. 1B, of one of, an aircraft 148, a spacecraft 150, an automotive vehicle 152, a watercraft 154, a train 156, a hospital 158, a factory building 160, an office building 162, a movie theater 164, a restaurant 166, or another suitable vehicle or structure.

As shown in FIG. 7, the method 300 further comprises the step of comparing 312, with the portable wand system 10, the positional data 58 against the depiction 34.

As shown in FIG. 7, the method 300 further comprises the step of determining 314, with the portable wand system 10, when the predetermined surface treatment application 14a (see FIG. 1A) is achieved with the surface treatment application element 16 for the one or more surfaces 12.

As shown in FIG. 7, the method 300 further comprises the step of activating 316, with the portable wand system 10, the indicator element 78 (see FIG. 1A) to signal to the user 52 that the predetermined surface treatment application 14a is achieved with the surface treatment application element 16 for the one or more surfaces 12.

The method 300 may further comprise after activating 316, with the portable wand system 10, the indicator element 78 to signal to the user 52 that the predetermined surface treatment application 14a is achieved, the steps of, moving the portable wand system 10 to a subsequent known location 132a (see FIG. 1A), to register the portable wand system 10 at the subsequent known location 132a, and repeating the steps of pressing 304 the user input button 24, measuring 306 the positional data 58, activating 318 the surface treatment application element 16, moving 310 the wand applicator 18 over the one or more surfaces 12, comparing 312 the positional data 58 against the depiction 34, determining 314 when the predetermined surface treatment application 14a is achieved, and activating 316 the indicator element 78 to signal to the user 52 that the predetermined surface treatment application 14a is achieved.

The step of activating 316 the indicator element 78 to signal to the user 52 that the predetermined surface treatment application 14a is achieved, may further comprise activating the indicator element 78 comprising a binary indicator 80 comprising, as shown in FIG. 1A, one of, a light signal 82 coupled to the wand applicator 18, a surface treatment application element flashing light alert 84, an audio alert 86, a sound alert 88, a tactile alert 90, a vibration alert 92, a pulsing alert 94, a pressure altering alert 96, or another suitable alert or alarm, to indicate that the surface treatment application 14, such as the predetermined surface treatment application 14a, of one or more of the one or more surfaces 12 is complete.

The step of activating 316 the indicator element 78 to signal to the user 52 that the predetermined surface treatment application 14a is achieved, may further comprise activating the indicator element 78 comprising a video display 98 coupled to the wand applicator 18, the video display 98 visible to the user 52 and showing one or more of, portions 102 (see FIG. 1A) of the one or more surfaces 12 to be surface treated, and a color coded signal 104 (see FIG. 1A), comprising a lighted progress bar 106 (see FIG. 1A), to indicate which portions 102 have complete coverage, that is, complete coverage portions 102a (see FIG. 1A).

Figure 8:
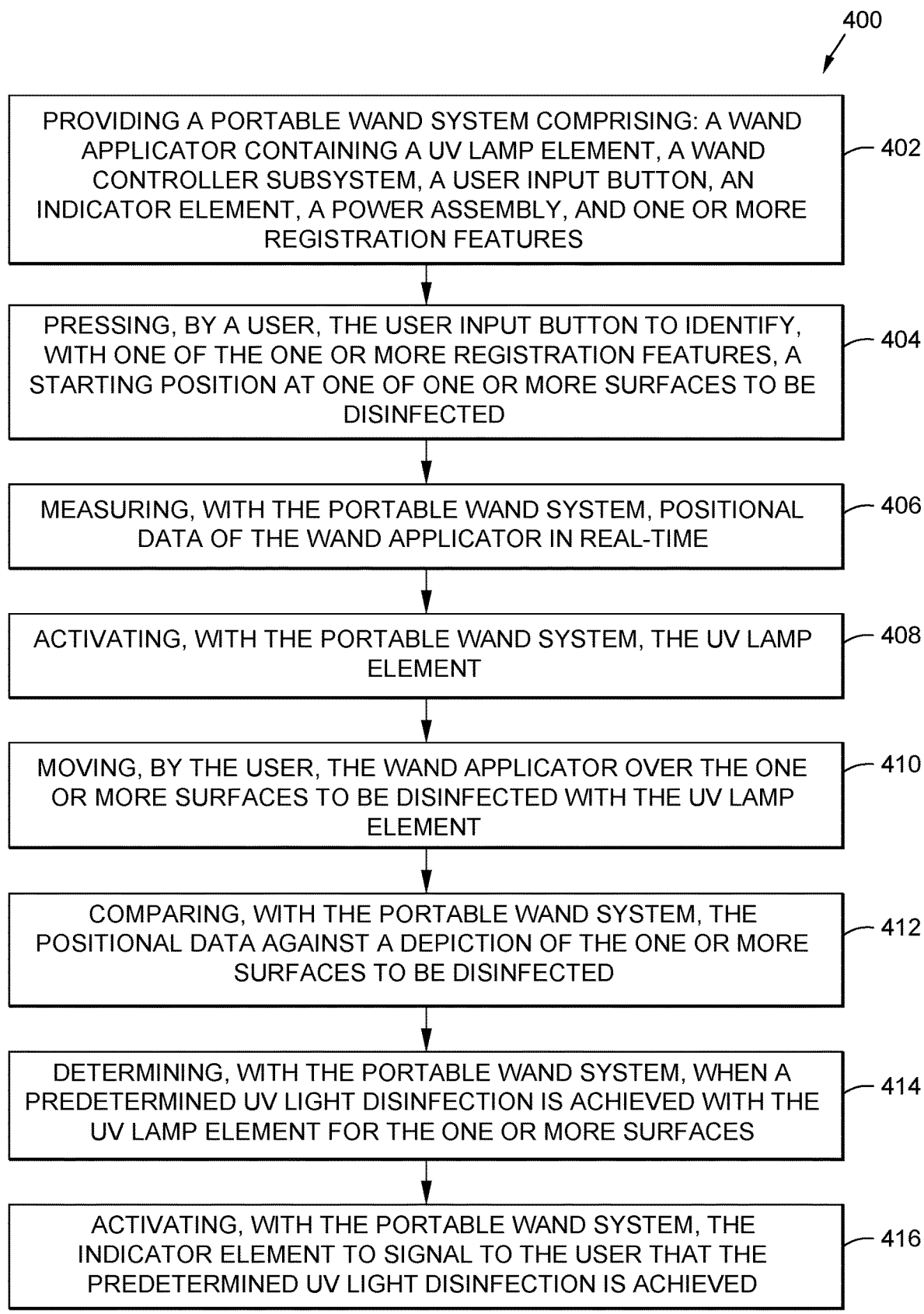
FIG. 8 is an illustration of a flow diagram of a version of another method of the disclosure.

Now referring to FIG. 8, FIG. 8 is an illustration of a flow diagram of a version of a method 400 of the disclosure. In another version of the disclosure, there is provided the method 400 for indicating to a user 52 when a predetermined ultraviolet (UV) light disinfection 172a (see FIG. 1B) is achieved for one or more surfaces 12 in an interior 146 (see FIG. 1B) of an aircraft 148 (see FIG. 1B).

The blocks in FIG. 8 represent operations and/or portions thereof, or elements, and lines connecting the various blocks do not imply any particular order or dependency of the operations or portions thereof, or elements. FIG. 8 and the disclosure of the steps of the method 400 set forth herein should not be interpreted as necessarily determining a sequence in which the steps are to be performed. Rather, although one illustrative order is indicated, it is to be understood that the sequence of the steps may be modified when appropriate. Accordingly, certain operations may be performed in a different order or simultaneously.

As shown in FIG. 8, the method 400 comprises the step of providing 402 a version of a portable wand system 10 (see FIGS. 1A, 2A-2B, 3A-3B, 5). As discussed in detail above, in one version, the portable wand system 10 comprises a wand applicator 18 (see FIG. 1A) containing a UV lamp element 26 (see FIG. 1A). The portable wand system 10 further comprises a wand controller subsystem 30 (see FIG. 1A) coupled to the wand applicator 18. The wand controller subsystem 30 comprises a computer program 32 (see FIG. 1A), such as an algorithm 32a (see FIG. 1A), and a depiction 34 (see FIG. 1A) of one or more surfaces 12 to be disinfected with the UV lamp element 26. The portable wand system 10 further comprises the user input button 24 (see FIG. 1A)

coupled to the wand applicator 18. The portable wand system 10 further comprises the indicator element 78 (see FIG. 1A).

The portable wand system 10 further comprises the power assembly 108 (see FIG. 1A) coupled to the wand applicator 18. The power assembly 108 may comprise the energy storage device 110, such as a battery 110a, coupled to the wand applicator 18, via the wired connector 114. The portable wand system 10 further comprises one or more registration features 130 (see FIG. 1A) to register the wand applicator 18 against one or more known locations 132 at the one or more surfaces 12 in the depiction 34, such as the geometric model 36, or photographic image 38.

The step of providing 402 the portable wand system 10 may further comprise, providing the portable wand system 10 comprising the computer recording system 136 (see FIG. 1A) coupled to the wand controller subsystem 30. The computer recording system 136 analyzes the positional data 58 of the wand applicator 18, and communicates to the indicator element 78 a status 173 (see FIG. 1B) of the UV light disinfection 172 (see FIG. 1B), such as the predetermined UV light disinfection 172a (see FIG. 1B), on the one or more surfaces 12. The computer recording system 136 comprises the computer 138 (see FIG. 1A) to record the surface treatment application 14 of the one or more surfaces 12, to validate and verify that the UV light disinfection 172, such as the predetermined UV light disinfection 172a, of the one or more surfaces 12 is correct.

The step of providing 402 the portable wand system 10 may further comprise providing the portable wand system 10 comprising the wand controller subsystem 30 with the depiction 34 of one or more surfaces 12 to be treated with the surface treatment application 14 comprising one of, a disinfection operation 168, an ultraviolet (UV) light disinfection operation 170, a decontamination operation 174, a sanitization operation 176, a sterilization operation 178, a curing operation 180, a shot peening operation 182, a chemical contaminant detection operation 184, a biological contaminant detection operation 186, a non-destructive inspection process 188, an eddy current crack detection 190, a paint application 192, an abrasive media blasting operation 194, a sand blasting operation 194a, a surface pre-heating operation 196, a torch welding operation 198, or another suitable surface treatment application.

The step of providing 402 the portable wand system 10 may further comprise providing the portable wand system 10 comprising the wand controller subsystem 30 with the depiction 34 comprising one of, a geometric model 36 of one or more surfaces 12 to be surface treated with the surface treatment application 14 of the surface treatment application element 16, and a photographic image 38 (see FIG. 1A) obtained with a photogrammetric process 40 (see FIG. 1A).

As shown in FIG. 8, the method 400 further comprises the step of pressing 404, by the user 52, the user input button 24 to identify, with one of the one or more registration features 130, a starting position 167 (see FIG. 1B) at one of the one or more surfaces 12 to be disinfected with the UV lamp element 26.

As shown in FIG. 8, the method 400 further comprises the step of measuring 406, with the portable wand system 10, positional data 58 (see FIG. 1A) of the wand applicator 18 in real-time.

As shown in FIG. 8, the method 400 further comprises the step of activating 408, with the portable wand system 10, the UV lamp element 26.

As shown in FIG. 8, the method 400 further comprises the step of moving 410, by the user 52, the wand applicator 18 over the one or more surfaces 12 to be disinfected with the UV lamp element 26.

The step of moving 410 the wand applicator 18 over the one or more surfaces 12 to be disinfected with the UV lamp element 26 may further comprise, moving the wand applicator 18 over the one or more surfaces 12 to be disinfected with the UV lamp element 26 emitting an ultraviolet (UV) light 28 (see FIG. 1A) having a wavelength in a range between 200 nanometers to 280 nanometers, to disinfect the one or more surfaces 12.

The step of moving 410 the wand applicator 18 over the one or more surfaces 12 to be disinfected with the UV lamp element 26 may further comprise, moving the wand applicator 18 over the one or more surfaces 12 to be disinfected with the UV lamp element 26 emitting an ultraviolet (UV) light 28 having a wavelength of 222 nanometers.

As shown in FIG. 8, the method 400 further comprises the step of comparing 412, with the portable wand system 10, the positional data 58 against the depiction 34.

As shown in FIG. 8, the method 400 further comprises the step of determining 414, with the portable wand system 10, when the predetermined UV light disinfection 172a (see FIG. 1B) is achieved with the UV lamp element 26 for the one or more surfaces 12.

As shown in FIG. 8, the method 400 further comprises the step of activating 416, with the portable wand system 10, the indicator element 78 (see FIG. 1A) to signal to the user 52 that the predetermined UV light disinfection 172a is achieved with the UV lamp element 26 for the one or more surfaces 12.

The method 400 may further comprise after activating 416, with the portable wand system 10, the indicator element 78 to signal to the user 52 that the predetermined UV light disinfection 172a is achieved, the steps of, moving the portable wand system 10 to a subsequent known location 132a (see FIG. 1A), to register the portable wand system 10 at the subsequent known location 132a, and repeating the steps of pressing 404 the user input button 24, measuring 406 the positional data 58, activating 408 the UV lamp element 26, moving 410 the wand applicator 18 over the one or more surfaces 12, comparing 412 the positional data 58 against the depiction 34, determining 414 when the predetermined UV light disinfection 172a is achieved, and activating 416 the indicator element 78 to signal to the user 52 that the predetermined UV light disinfection 172a is achieved.

The step of activating 416 the indicator element 78 to signal to the user 52 that the predetermined UV light disinfection 172a is achieved, may further comprise activating the indicator element 78 comprising a binary indicator 80 comprising, as shown in FIG. 1A, one of, a light signal 82 coupled to the wand applicator 18, a UV lamp element flashing light alert 84a, an audio alert 86, a sound alert 88, a tactile alert 90, a vibration alert 92, a pulsing alert 94, a pressure altering alert 96, or another suitable alert or alarm, to indicate the predetermined UV light disinfection 172a of one or more of the one or more surfaces 12 is complete.

The step of activating 416 the indicator element 78 to signal to the user 52 that the predetermined UV light disinfection 172a is achieved, may further comprise activating the indicator element 78 comprising a video display 98 coupled to the wand applicator 18, the video display 98 visible to the user 52 and showing one or more of, portions 102 (see FIG. 1A) of the one or more surfaces 12 to be disinfected, and a color coded signal 104 (see FIG. 1A), comprising a lighted progress bar 106 (see FIG. 1A), to indicate which portions 102 have complete coverage, that is, complete coverage portions 102a (see FIG. 1A).

As an example of using the method 400 (see FIG. 8), a user 52 or operator 54 places the wand applicator 18 with the UV lamp element 26 in a known location 132, or datum, such as an arm rest 250 (see FIG. 4) of a seat 248 (see FIG. 4) in a cabin 246 (see FIG. 4) of an aircraft 148 (see FIG. 1B), based on a depiction 23, such as a geometric model 36. The user 52 or operator 54 pushes the user input button 24 on the handle portion 20 of the wand applicator 18, to identify the starting position 167 (see FIG. 1B).

As the wand applicator 18 is lifted up, the accelerometer 46 (see FIG. 1A) registers movement in the z direction, for example, 4 (four) inches above the arm rest 250. The UV lamp element 26 is turned on, and the wand applicator 18 is moved in the y direction, for example, 20 (twenty) inches over to another arm rest 250 in the same row as the starting position 167 arm rest 250. The wand controller subsystem 30 sends positional data 58 (see FIG. 1A), based on the geometric model 36, wirelessly to a computer 138 (see FIG. 1A), that may be located on the aircraft 148, or in a remote location.

Based on the height of the wand applicator 18, a lateral position of the wand applicator 18, an orientation of the wand applicator 18, and a duration and output of the UV lamp element 26, the portable wand system 10 uses a computer program 32, such as an algorithm 32a, to determine when sufficient UV light 28 has been emitted or irradiated to disinfect the surface 12 of interest.

The computer 138 communicates to the indicator element 78, such as a binary indicator 80, which activates a light signal 82 (see FIG. 1A), a sound alert 88 (see FIG. 1A), or another suitable alert or alarm, to signal that the UV light disinfection 172 (see FIG. 1B) is complete for that surface 12 in that area. As an alternative, or in addition to, the binary indicator 80, the portable wand system 10 may comprise a video display 98 to show a surface 12 or an area of the surfaces 12 or areas to be surface treated, such as disinfected or cleaned, or a color coded signal 104 (see FIG. 1A), such as a lighted progress bar 106 (see FIG. 1A).

As the user 52 or operator 54 moves the wand applicator 18 to a new surface 12 or location, the process is repeated. The UV light disinfection operation 170 (see FIG. 1B) may be recorded on the computer 138 of the computer recording system 136 as validation of the disinfection operation 168 of the surface 12 and the area.

Figure 9:
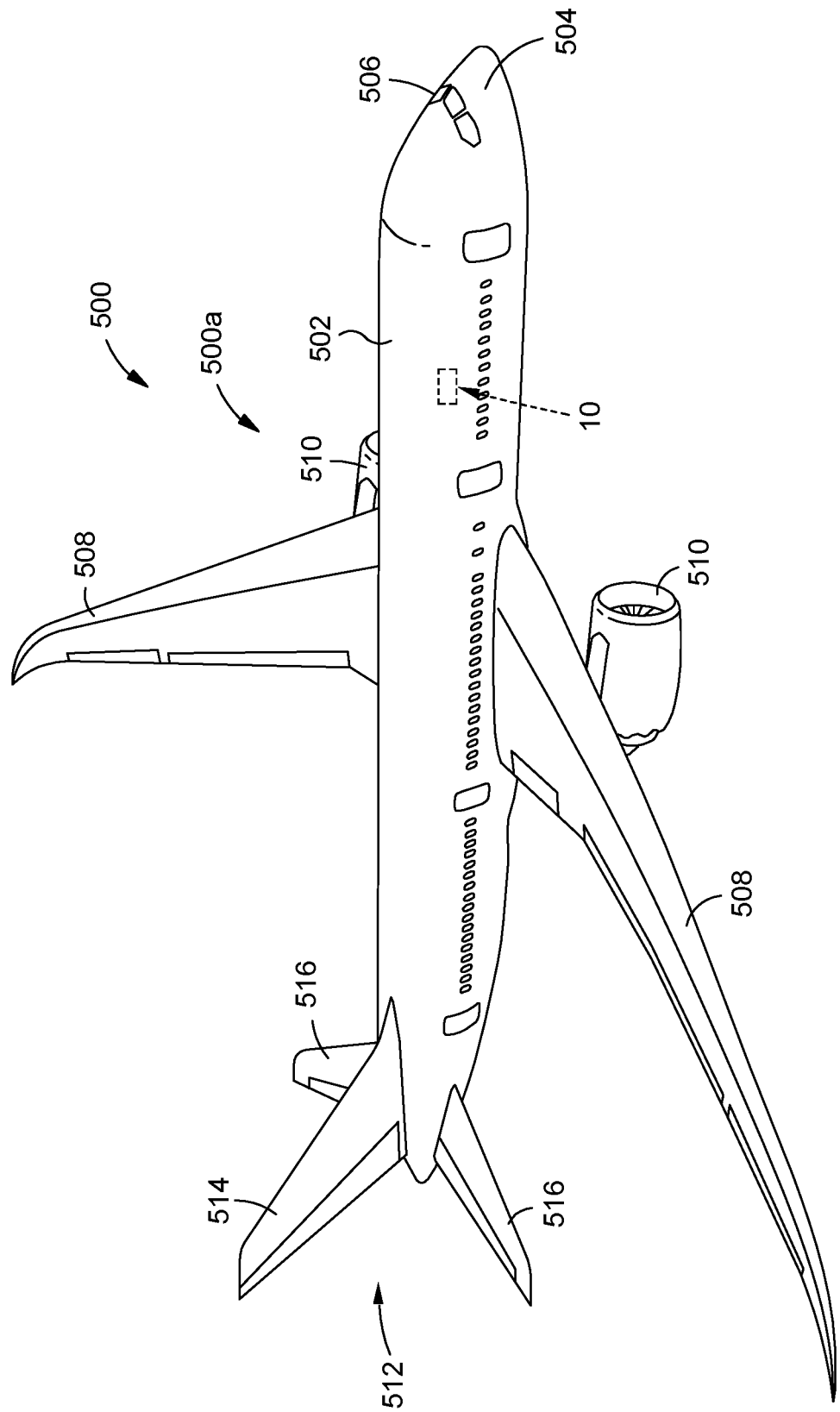
FIG. 9 is an illustration of a perspective view of an aircraft that may use a portable wand system of the disclosure.

Now referring to FIG. 9, FIG. 9 is an illustration of a perspective view of an air vehicle 500, such as an aircraft 500a, that may use a version of a portable wand system 10 (see FIGS. 1A, 2A-2B) of the disclosure. As shown in FIG. 9, the air vehicle 500, such as the aircraft 500a, includes a fuselage 502, a nose 504, a cockpit 506, wings 508, engines 510, and a tail 512. As shown in FIG. 9, the tail 512 comprises a horizontal stabilizer portion 514 and vertical stabilizer portions 516. The portable wand system 10 shown and described with respect to FIGS. 1A, 2A-2B, 3A-3B, and 5A may be used to disinfect, sanitize, sterilize, or perform another surface treatment application 14 on various surfaces, structures, objects, and components within the aircraft 500a, including inside the cockpit 506 or flight deck, inside the cabin 246 (see FIG. 4), inside a galley area, inside a bathroom, inside a closet, and inside stowage bins.

Figure 10:
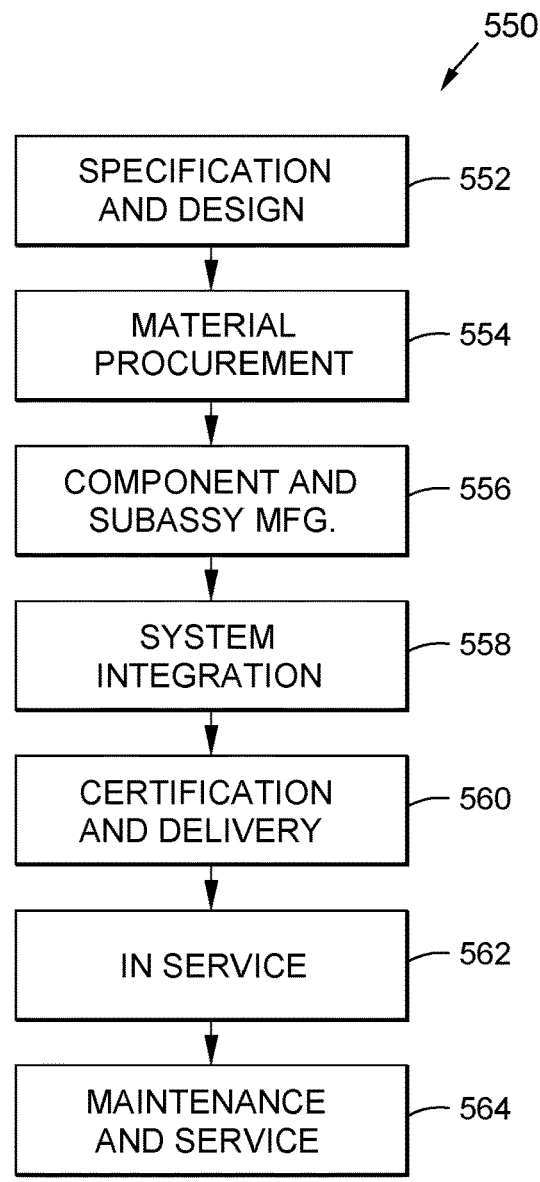
FIG. 10 is an illustration of a flow diagram of an exemplary aircraft manufacturing and service method.
Figure 11:
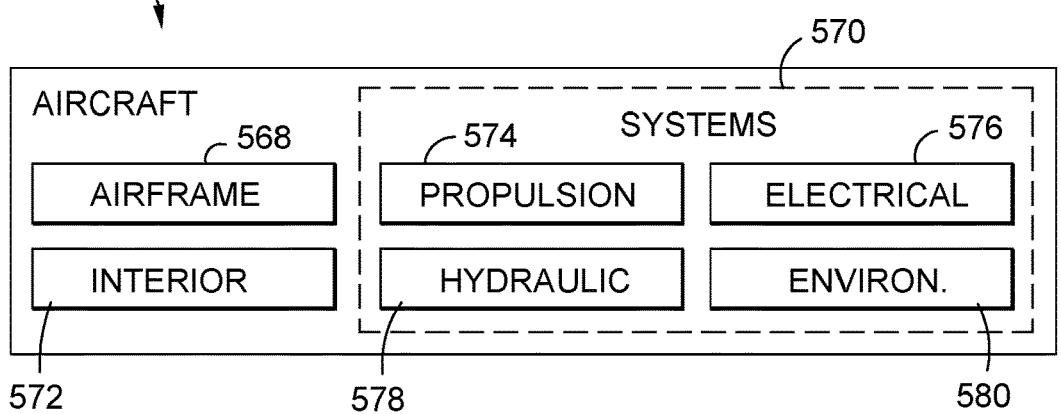
FIG. 11 is an illustration of an exemplary block diagram of an aircraft.

Now referring to FIGS. 10 and 11, FIG. 10 is an illustration of a flow diagram of an exemplary aircraft manufacturing and service method 550, and FIG. 11 is an illustration of an exemplary block diagram of an aircraft 566. Referring to FIGS. 10 and 11, versions of the disclosure may be described in the context of the aircraft manufacturing and service method 550 as shown in FIG. 10, and the aircraft 566 as shown in FIG. 11.

During pre-production, exemplary aircraft manufacturing and service method 550 may include specification and design 552 of the aircraft 566 and material procurement 554. During manufacturing, component and subassembly manufacturing 556 and system integration 558 of the aircraft 566 takes place. Thereafter, the aircraft 566 may go through certification and delivery 560 in order to be placed in service 562. While in service 562 by a customer, the aircraft 566 may be scheduled for routine maintenance and service 564 (which may also include modification, reconfiguration, refurbishment, and other suitable services).

Each of the processes of the aircraft manufacturing and service method 550 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 11, the aircraft 566 produced by the exemplary aircraft manufacturing and service method 550 may include an airframe 568 with a plurality of systems 570 and an interior 572. Examples of the plurality of systems 570 may include one or more of a propulsion system 574, an electrical system 576, a hydraulic system 578, and an environmental system 580. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 550. For example, components or subassemblies corresponding to component and subassembly manufacturing 556 may be fabricated or manufactured in a manner similar to components or subassemblies produced while the aircraft 566 is in service 562. Also, one or more apparatus embodiments, method embodiments, or a combination thereof, may be utilized during component and subassembly manufacturing 556 and system integration 558, for example, by substantially expediting assembly of or reducing the cost of the aircraft 566. Similarly, one or more of apparatus embodiments, method embodiments, or a combination thereof, may be utilized while the aircraft 566 is in service 562, for example and without limitation, to maintenance and service 564.

Disclosed versions of the portable wand system 10 (see FIGS. 1A, 2A-2B, 3A-3B, 5A), the method 300 (see FIG. 7) and the method 400 (see FIG. 8) measure the position, orientation, duration, and output of the wand applicator 18 in real-time, and by comparing these with a depiction 34 (see FIG. 1A), such as a geometric model 36 (see FIG. 1A) of the area and map of desired or predetermined exposure or dispensing coverage, indicates to the user 52 when the desired or predetermined exposure, or minimum desired exposure, has been achieved for a particular surface 12 or area. The indication to the user 52 may be an indicator element 78 comprising a binary indicator 80 or a video display 98 visible to the user 52 showing areas of the object or area to be covered, color coded to indicate which areas have complete coverage. The portable wand system 10 utilizes the high dexterity of a user 52, such as a human operator, while achieving the traceability and repeatability of an automated process. Disclosed versions of the portable wand system 10 (see FIGS. 1A, 2A-2B, 3A-3B, 5A), the method 300 (see FIG. 7) and the method 400 (see FIG. 8) indicate, validate, and verify the proper and thorough application of a surface treatment application 14, such as a UV light disinfection operation 170 (see FIG. 1B), onto the surfaces 12 of an environment or object. By recording this information with the computer recording system 136 (see FIG. 1A) over the entire surface treatment session, such as a disinfecting or cleaning session, a larger, overall area treatment validation may be accomplished for quality control purposes.

Moreover, disclosed versions of the portable wand system 10 (see FIGS. 1A, 2A-2B, 3A-3B, 5A), the method 300 (see FIG. 7) and the method 400 (see FIG. 8) allow verification and validation to operators 54 in real-time and to inspectors 56 (see FIG. 1A), such as independent inspectors, after the surface treatment applications 14, such as predetermined surface treatment applications 14a, are complete, that disinfection, sanitization, decontamination, or another surface treatment application 14, or process, requiring a minimum surface exposure has been achieved for one or more surfaces 12 of an area or object. The portable wand system 10 also allows the user 52 (see FIG. 1A), such as an operator 54 (see FIG. 1A), to self-verify that the surface treatment application 14 has been sufficiently performed and completed. Additionally, the portable wand system 10 indicates the sufficiency of other processes, such as curing operations 180 (see FIG. 1B), such as a curing operation of a surface coating 180a (see FIG. 1B), or UV curing of surface coatings, a shot peening operation 182 (see FIG. 1B), such as a shot peening operation of a metallic surface 182a (see FIG. 1B), a chemical contaminant detection operation 184 (see FIG. 1B), a biological contaminant detection operation 186 (see FIG. 1B), a non-destructive inspection processes 188 (see FIG. 1B), such as an eddy current crack detection 190 (see FIG. 1B), or another suitable surface treatment application.

Disclosed versions of the portable wand system 10 (see FIGS. 1A, 2A-2B, 3A-3B, 5A), the method 300 (see FIG. 7) and the method 400 (see FIG. 8) provide a high degree of repeatability, a high degree of quality control, a high degree of efficiency, and an improved consistency to produce a high quality surface treatment application 14, while keeping the dexterity of users 52 performing the surface treatment application 14, as opposed to automated methods requiring highly complex equipment that are less dexterous than a human operator, when a complex surface is to be treated. The portable wand system 10 enables the adaptability of a human operator, with the traceability of automated processes, but without the complexity. The portable wand system 10 provides a surface treatment application 14, such as a disinfection operation 168, that validates and verifies that the surface treatment application 14, such as the disinfection operation 168, has been achieved for a surface 12 using the wand applicator 18, such as a handheld wand applicator 18a (see FIG. 1A).

The portable wand system 10 utilizes a 6 degrees of freedom inertial measurement unit 42a (see FIG. 1A), or one or more, either separately, or in combination, of a fixed position extensometer 72 (see FIG. 1A), a rotary position sensor 74 (see FIG. 1A), and/or an external photogrammetric sensor 76 (see FIG. 1A), to determine the position 50 of the wand applicator 18. A depiction 34, such as a geometric model 36, or photographic image 38 taken with a photogrammetric process 40, of the area or object to be treated, is used with the surfaces 12 and surface treatment application 14 exposure or treatment flux (UV exposure per area), acceleration, and duration superimposed on the depiction 34. In a preferred version, the portable wand system 10 has a wand applicator 18 containing a UV lamp element 26, such as a 222 nm (nanometer) UV lamp element 26a. The portable wand system 10 verifies and validates the correct application of 222 nm UV light emission onto surfaces 12 for UV light disinfection 172 (see FIG. 1B).

Many modifications and other versions of the disclosure will come to mind to one skilled in the art to which this disclosure pertains having the benefit of the teachings presented in the foregoing descriptions and the associated drawings. The versions described herein are meant to be illustrative and are not intended to be limiting or exhaustive. Although specific terms are employed herein, they are used in a generic and descriptive sense only and not for purposes of limitation.

What is claimed is:

1. A portable wand system comprising:

a wand applicator containing a surface treatment application element;

a wand controller subsystem coupled to the wand applicator, the wand controller subsystem comprising, a computer program, a 6 degrees of freedom inertial measurement unit (IMU), a central processing unit (CPU) coupled to the IMU, a surface treatment application element power feedback to the CPU, a memory unit coupled to the CPU, and a provided CAD (computer-aided design) model of an area with one or more surfaces to be surface treated in an interior of an aircraft with a surface treatment application of the surface treatment application element and a map of a predetermined surface treatment application of the one or more surfaces to be surface treated in the interior of an aircraft, the 6 degrees of freedom IMU measuring one or more positions of the wand applicator as it is moved by a user over the one or more surfaces to be surface treated in the interior of the aircraft;

a user input button coupled to the wand applicator;

an indicator element to indicate that the surface treatment application of one or more of the one or more surfaces in the interior of the aircraft is complete;

a power assembly coupled to the wand applicator;

one or more registration features to periodically register the wand applicator against one or more known locations and one or more known orientations at the one or more surfaces in the interior of the aircraft in the provided CAD model, the one or more known locations comprising one or more of, a starting position known location and one or more subsequent known locations, and when the user presses the user input button, the one or more registration features identify the starting position known location at one of the one or more surfaces to be surface treated in the interior of the aircraft; and a computer recording system coupled to the wand controller subsystem, the computer recording system operable to analyze positional data of the wand applicator, and operable to communicate to the indicator element a status of the predetermined surface treatment application on the one or more surfaces in the interior of the aircraft, the computer recording system comprising a computer to record the predetermined surface treatment application of the one or more surfaces, to validate and verify that the predetermined surface treatment application is correct and complete, wherein the portable wand system measures the positional data, orientation, duration, and output of the wand applicator in real-time, and compares the positional data against the provided CAD model, to indicate to the user when the predetermined surface treatment application is achieved for the one or more surfaces in the interior of the aircraft.

2. The portable wand system of claim 1, wherein the computer program determines when a sufficient surface treatment application has been applied to surface treat the one or more surfaces in the interior of the aircraft, based on a height of the wand applicator from the one or more surfaces to be surface treated, a lateral position of the wand applicator, an orientation of the wand applicator, and a duration and an output of the surface treatment application element.

3. The portable wand system of claim 1, wherein the surface treatment application element comprises one of, an ultraviolet (UV) lamp element, a gaseous dispersal element, an aerosolized element, a disinfectant fluid, a disinfectant gas, a sanitizing fluid, a sanitizing gas, a sterilizing fluid, a sterilizing gas, a cleaning solution, a curing element, a shot peening element, a contamination detection element, a paint, an abrasive media blasting element, a sand blasting element, a surface pre-heating element, and a torch welding element.

4. The portable wand system of claim 1, wherein the surface treatment application comprises one of, a disinfection operation, an ultraviolet (UV) light disinfection operation, a decontamination operation, a sanitization operation, a sterilization operation, a curing operation, a shot peening operation, a chemical contaminant detection operation, a biological contaminant detection operation, a non-destructive inspection process, an eddy current crack detection, a paint application, an abrasive media blasting operation, a sand blasting operation, a surface pre-heating operation, and a torch welding operation.

5. The portable wand system of claim 1, wherein the 6 degrees of freedom inertial measurement unit (IMU) further comprises an integrated circuit and an accelerometer.

6. The portable wand system of claim 1, wherein the wand controller subsystem further comprises a wireless network interface coupled to the central processing unit (CPU).

7. The portable wand system of claim 1, wherein the surface treatment application is a predetermined ultraviolet (UV) light disinfection having:
a level of treatment in a range of 2 millijoules per square centimeter to 100 millijoules per square centimeter irradiance of UV light;
a traversing speed of the wand applicator in a range of 1 inch per second to 10 inches per second; and
a distance the wand applicator is held by the user from the surface to be surface treated in a range of 1 inch to 6 inches.

8. The portable wand system of claim 1, wherein the indicator element comprises a binary indicator comprising one of, a light signal coupled to the wand applicator, a surface treatment application element flashing light alert, an audio alert, a sound alert, a tactile alert, a vibration alert, a pulsing alert, a pressure altering alert, to indicate the predetermined surface treatment application of one or more of the one or more surfaces is complete.

9. The portable wand system of claim 1, wherein the indicator element comprises a video display coupled to the wand applicator, the video display visible to the user and showing one or more of, portions of the one or more surfaces to be surface treated, and a color coded signal, comprising a lighted progress bar, to indicate which portions have complete coverage.

10. The portable wand system of claim 1, wherein the one or more registration features comprise arm rests of seats in the interior of the aircraft.

11. A portable wand system for disinfecting one or more surfaces in an interior of an aircraft, the portable wand system comprising:
a wand applicator containing an ultraviolet (UV) lamp element;
a wand controller subsystem coupled to the wand applicator, the wand controller subsystem comprising, a computer program, a 6 degrees of freedom inertial measurement unit (IMU), a central processing unit (CPU) coupled to the IMU, an ultraviolet (UV) lamp element power feedback to the CPU, a memory unit coupled to the CPU, and a provided CAD (computer-aided design) model of an area with the one or more surfaces in the interior of the aircraft to be disinfected with the UV lamp element and a map of a predetermined ultraviolet (UV) light disinfection of the one or more surfaces in the interior of the aircraft to be disinfected, the 6 degrees of freedom IMU measuring one or more positions of the wand applicator as it is moved by a user over the one or more surfaces to be disinfected in the interior of the aircraft;
a user input button coupled to the wand applicator;
an indicator element to indicate that the disinfecting of one or more of the one or more surfaces in the interior of the aircraft is complete;
a power assembly coupled to the wand applicator;
one or more registration features to periodically register the wand applicator against one or more known locations and one or more known orientations at the one or more surfaces in the interior of the aircraft in the provided CAD model, the one or more known locations comprising one or more of, a starting position known location and one or more subsequent known locations, and when the user presses the user input button, the one or more registration features identify the starting position known location at one of the one or more surfaces in the interior of the aircraft to be disinfected; and
a computer recording system coupled to the wand controller subsystem, the computer recording system operable to analyze positional data of the wand applicator, and operable to communicate to the indicator element a status of the predetermined UV light disinfection of the one or more surfaces in the interior of the aircraft with the UV lamp element, the computer recording system comprising a computer to record the predetermined UV light disinfection of the one or more surfaces, to validate and verify that the predetermined UV light disinfection is correct and complete,
wherein the portable wand system measures the positional data, orientation, duration, and output of the wand applicator in real-time, and compares the positional data against the provided CAD model, to indicate to the user when the predetermined ultraviolet (UV) light disinfection is achieved for the one or more surfaces in the interior of the aircraft.

12. The portable wand system of claim 11, wherein the computer program determines when a sufficient UV light disinfection has been emitted to disinfect the one or more surfaces in the interior of the aircraft, based on a height of the wand applicator from the one or more surfaces to be disinfected, a lateral position of the wand applicator, an orientation of the wand applicator, and a duration and an output of the UV lamp element.

13. The portable wand system of claim 11, wherein the UV lamp element is operable to emit an ultraviolet (UV) light having a wavelength in a range between 200 nanometers to 280 nanometers, to disinfect the one or more surfaces.

14. The portable wand system of claim 11, wherein the wand controller subsystem further comprises a wireless network interface coupled to the central processing unit (CPU).

15. The portable wand system of claim 11, wherein the indicator element comprises one of, a binary indicator coupled to the wand applicator, and a video display coupled to the wand applicator.

16. A method for indicating to a user when a predetermined ultraviolet (UV) light disinfection is achieved for one or more surfaces in an interior of an aircraft, the method comprising the steps of:
providing a portable wand system comprising:
a wand applicator containing an ultraviolet (UV) lamp element;
a wand controller subsystem coupled to the wand applicator, the wand controller subsystem comprising, a computer program, a 6 degrees of freedom inertial measurement unit (IMU), a central processing unit (CPU) coupled to the IMU, a surface treatment application element power feedback to the CPU, a memory unit coupled to the CPU, and a provided CAD (computer-aided design) model of an area with the one or more surfaces in the interior of the aircraft to be disinfected with the UV lamp element and a map of the predetermined UV light disinfection of the one or more surfaces in the interior of the aircraft to be disinfected, the 6 degrees of freedom IMU measuring one or more positions of the wand applicator as it is moved by the user over the one or more surfaces in the interior of the aircraft to be disinfected;
a user input button coupled to the wand applicator;
an indicator element to indicate that disinfecting of one or more of the one or more surfaces in the interior of the aircraft is complete;
a power assembly coupled to the wand applicator;
one or more registration features to periodically register the wand applicator against one or more known locations and one or more known orientations at the one or more surfaces in the interior of the aircraft in the provided CAD model, the one or more known locations comprising one or more of, a starting position known location and one or more subsequent known locations, and when the user presses the user input button, the one or more registration features identify the starting position known location at one of the one or more surfaces in the interior of the aircraft to be disinfected; and
a computer recording system coupled to the wand controller subsystem, the computer recording system analyzing positional data of the wand applicator, and communicating to the indicator element a status of the predetermined UV light disinfection at the one or more surfaces, the computer recording system comprising a computer to record the predetermined UV light disinfection of the one or more surfaces, to validate and verify that the predetermined UV light disinfection is correct and complete,
pressing, by the user, the user input button to identify, with one of the one or more registration features, the starting position known location at one of the one or more surfaces in the interior of the aircraft to be disinfected;
measuring, with the portable wand system, the positional data, orientation, duration, and output of the wand applicator in real-time;
activating, with the portable wand system, the UV lamp element;
moving, by the user, the wand applicator over the one or more surfaces in the interior of the aircraft to be disinfected with the UV lamp element;
comparing, with the portable wand system, the positional data against the provided CAD model;
determining, with the portable wand system, when the predetermined UV light disinfection is achieved with the UV lamp element for the one or more surfaces in the interior of the aircraft; and
activating, with the portable wand system, the indicator element to signal to the user that the predetermined UV light disinfection is achieved with the UV lamp element for the one or more surfaces in the interior of the aircraft.

17. The method of claim 16, further comprising, after activating, with the portable wand system, the indicator element to signal to the user that the predetermined UV light disinfection is achieved, the steps of:
moving the portable wand system to one of the one or more subsequent known locations, to register the portable wand system at the subsequent known location; and
repeating the steps of pressing the user input button, measuring the positional data, activating the UV lamp element, moving the wand applicator over the one or more surfaces, comparing the positional data against the provided CAD model, determining when the predetermined UV light disinfection is achieved, and activating the indicator element to signal to the user that the predetermined UV light disinfection is achieved.

18. The method of claim 16, wherein the step of providing the portable wand system further comprises, providing the portable wand system comprising the computer program that determines when a sufficient UV light disinfection has been emitted to disinfect the one or more surfaces in the interior of the aircraft, based on a height of the wand applicator from the one or more surfaces to be disinfected, a lateral position of the wand applicator, an orientation of the wand applicator, and a duration and an output of the UV lamp element.

19. The method of claim 16, wherein the step of moving the wand applicator over the one or more surfaces to be disinfected with the UV lamp element further comprises, moving the wand applicator over the one or more surfaces to be disinfected with the UV lamp element emitting an ultraviolet (UV) light having a wavelength in a range between 200 nanometers to 280 nanometers, to disinfect the one or more surfaces.

20. The method of claim 16, wherein the step of activating the indicator element to signal to the user that the predetermined UV light disinfection is achieved, further comprises activating the indicator element comprising one of, a binary indicator coupled to the wand applicator, and a video display coupled to the wand applicator.

* * * * *